United States Patent [19]
Dunsmuir et al.

[11] Patent Number: 5,945,580
[45] Date of Patent: Aug. 31, 1999

[54] CAPSICUM HEMICELLULASE POLYNUCLEOTIDES AND POLYPEPTIDES

[75] Inventors: Pamela Dunsmuir, Piedmont; Mark H. Harpster, Albany, both of Calif.

[73] Assignee: DNA Plant Technology Corporation, Oakland, Calif.

[21] Appl. No.: 08/635,066

[22] Filed: Apr. 19, 1996

[51] Int. Cl.⁶ .............................. A01H 5/00; A01H 5/10; C12N 5/14; C12N 15/29
[52] U.S. Cl. ...................... 800/298; 435/320.1; 435/419; 435/468; 536/23.2; 536/23.6; 800/278; 800/317.1; 800/317.4
[58] Field of Search .............................. 435/320.1, 172.3, 435/419, DIG. 43; 536/23.2, 23.6, 24.1; 800/205, 250, DIG. 9, DIG. 40, DIG. 41, DIG. 44, DIG. 52

[56] References Cited

U.S. PATENT DOCUMENTS 5,328,999  7/1994  Bennett et al. ........................ 536/24.5

OTHER PUBLICATIONS

Casadoro G (A). GenBank Accession No. X83709, Jan. 6, 1995.
Casadoro G (B). GenBank Accession No. X97188, Apr. 9, 1996.
Sambrook J, et al. "Molecular Cloning: A Laboratory Manual." Cold Spring Harbor Laboratory Press, NY, pp. 8.46–8.52, 1989.
Smith CJS, et al. "Antisense RNA inhibition of polygalacturonase gene expression in transgenic tomatoes." Nature 334: 724–726, 1988.

*Primary Examiner*—Douglas W. Robinson
*Assistant Examiner*—Amy J. Nelson
*Attorney, Agent, or Firm*—Townsend and Townsend and Crew LLP

[57] ABSTRACT

The invention provides polynucleotides of the *Capsicum annuum* hemicellulase gene, and compositions and uses thereof for controlling plant development and other characteristics.

15 Claims, 5 Drawing Sheets

Figure 1A 1   gaattcaaattatgttaagagtttgtggagtctacacatcataaacctgaattatgcctatatgaattatgcctatataagggggggggggc
    *
93  aaatcaaaaagtattcataagagatcaaactctctcatcttgataatcatatatacacaaaccctctcctttatggagatcaaatcc 185 aaatagtcttactttcgagaaataacggccgaaaattcatatcaaatcCTAATATACCTACATTGAAAAATACGCTACTGACGATCCTCG 277 AATTACGGAGAAATTTATATCAAATTCAAATATTCCTACGTTCAAAAAATACACTATTGACGGCCCTCGAATTATGAAGAAATCAAGAGAG 369 AAACTGATTTATGTCCATATTGTTTATCAATAAAAAATTATGTTTTTTCATATTTTAATTGTGATTGCAATTATTATTGTGTAAAAAAAA 461 TTGTGGGAAACAAAAATCTCTAATAGGCAATAGCTCACATGCCCTATAAATACCACCATAACATTATCAAACTTTCTAACATATAGACATAA
                                                      *
553 ATATTAAATAGTCATAAACCATATATGTTATATAATAATATATATATAATA ATG GCT TGT TCA ACG AAT ATT TGG GTT
                                                      1 ▶Met Ala Cys Ser Thr Asn Ile Trp Val
                                                           →

636 GTT ATA TTC TTC TTG TGC TTA TTA GCT GGT CCA ATT ATT GCT CAA GAT TAT AAA GAT GCA CTT GGC AAA
10 ▶Val Ile Phe Phe Leu Cys Leu Leu Ala Gly Pro Ile Ile Ala Gln Asp Tyr Lys Asp Ala Leu Gly Lys

705 TCT ATT TTA TTT TTT GAA GGA CAA CTG CCA AGA CGT TCT GGG AGA GTC CAA AGA TCT CAA AGA TGG AGA GGA
33 ▶Ser Ile Leu Phe Phe Glu Gly Gln Arg Ser Gly Arg Val Ser Gln Arg Leu Pro Val Ser Gln Arg Val Lys Trp Arg Gly

774 GAT TCT GCA CTC ATT GAT GCC AAA ATT GAA CAT GTG AAC TTA ATT GGC TAC TAT GAT GCT GGT GAC
56 ▶Asp Ser Ala Leu Ile Asp Ala Lys Ile Glu His Val Asn Leu Ile Gly Tyr Tyr Asp Ala Gly Asp

843 AAC GTG AAA TTT GGA TGG CCC ATG GCT TTT TCT TTA ACT TTA TTG AGT TGG GCT GCT ATT GAA TAC CCA
79 ▶Asn Val Lys Phe Gly Trp Pro Met Ala Phe Ser Leu Thr Leu Leu Ser Trp Ala Ala Ile Glu Tyr Pro

Figure 1B

```
 912 ACA CAA ATC TCT TCT GCA AAC CAA CTT CCC CAC CTC CAA CGT GCA ATT CGA TGG GGC ACA AAT TTC TTA
 102,Thr Gln Ile Ser Ser Ala Asn Gln Leu Pro His Leu Gln Arg Ala Ile Arg Trp Gly Thr Asn Phe Leu

981 ATT CGA GCC CAT ACT TCA ACT ACC ACT CTC TAT ACT CAG GTT GGA GAT GCA GAT GGA AAT GCA GAT CAC CAA TGT
 125,Ile Arg Ala His Thr Ser Thr Thr Thr Leu Tyr Thr Gln Val Gly Asp Ala Asp Gly Asn Ala Asp His Gln Cys

1050 TGG GAG AGA CCA GAA ATG GAT ACA CCA AGA ACA TTA TAT AAA ATC ACA TCA AAT TCT CCA GGT TCT
 148,Trp Glu Arg Pro Glu Met Asp Thr Pro Arg Thr Leu Tyr Lys Ile Thr Ser Asn Ser Pro Gly Ser

1119 GAG GTT GCA GCT GAA GTA GCT GCT GCT TTT GCT GCT GCG TCT ATT GTT TTC AAA AAT ATT GAT TCC AAT
 171,Glu Val Ala Ala Glu Val Ala Ala Ala Phe Ala Ala Ala Ser Ile Val Phe Lys Asn Ile Asp Ser Asn

1188 TAC TCT GCT AAA TTA AGA AGA TCC CAA TCT CTA GCA TTT GCG GAC AAG TAT AGA GGA TCT TAC
 194,Tyr Ser Ala Lys Leu Arg Arg Ser Gln Ser Leu Phe Ala Asp Lys Tyr Arg Gly Ser Tyr

1257 CAG GCT TCT TGC CCA TTC TAC TGC TCT TAC TCA GGT TAT TCA GAT GAA TTG TTG TGG GCT GCT GCA TGG
 217,Gln Ala Ser Cys Pro Phe Tyr Cys Ser Tyr Ser Gly Tyr Gln Asp Glu Leu Leu Trp Ala Ala Ala Trp

1326 CTA TAC AAG GCA GGT GGA GGA AAC AAT TAT GCT TTA AAC TAT GGA GCC CAA ATT TTA CTA GCC AAG GAG TTT CTT AAT
 240,Leu Tyr Lys Ala Gly Gly Gly Asn Asn Tyr Ala Leu Asn Tyr Gly Ala Gln Ile Leu Leu Ala Lys Glu Phe Leu Asn

1395 CCC TCT GAA TTC AGT TGG GAT TGG GAT AAC AAG TTC AAG GAT GCT GAT TCA TTT GTT TGT GCA TTA ATG CCA GGA AGT
 263,Pro Ser Glu Phe Ser Trp Asp Trp Asp Asn Lys Phe Lys Asp Ala Asp Ser Phe Val Cys Ala Leu Met Pro Gly Ser

1464 GGG AAG AGC AAT CTG GAA AAG ACA ATT CAG AAA GAT GCT GGA CTA TTG TTT TTT AGA GAT AGC AAT TTG CAA TAT
 286,Gly Lys Ser Asn Leu Glu Lys Thr Ile Gln Lys Asp Ala Gly Leu Leu Phe Phe Arg Asp Ser Asn Leu Gln Tyr

1533 AGC TCT GTA CAG ATT AAG ACA ACC CCG GGT GGA CTA TTG
 309,Ser Ser Val Gln Ile Lys Thr Thr Pro Gly Gly Leu Leu
```

Figure 1C

```
1602 GTG TCT GGT GCC ACC ATG GTA CTT TTT ATG TAC TCT AAA GTC CTT GAT GCA GCT GGA AAA GAG GGA ATT
 332,Val Ser Gly Ala Thr Met Val Leu Phe Met Tyr Ser Lys Val Leu Asp Ala Ala Gly Lys Glu Gly Ile

1671 ACA TGT GGA TCT GTT AAT TTT TCC ACC TCC AAG ATT AAA GCC TTT GCA AAA TCA CAG GTA GAC TAC ATA
 355,Thr Cys Gly Ser Val Asn Phe Ser Thr Ser Lys Ile Lys Ala Phe Ala Lys Ser Gln Val Asp Tyr Ile

1740 CTT GGT AAC AAT CCA CTT CAA ATG TCA TAC ATG TCT GGA TTT GGC AAC AAA TAC CCA ACA CAA CTC CAC
 378,Leu Gly Asn Asn Pro Leu Gln Met Ser Tyr Met Val Gly Phe Gly Asn Lys Tyr Pro Thr Gln Leu His

1809 CAT AGA GCC TCA TCA CTT CCT TCA ATT TAT AAC CAC CCC ACC AGG GTG GGC TGC AAC GAT GGC TAT AGT
 401,His Arg Ala Ser Ser Leu Pro Ser Ile Tyr Asn His Pro Thr Arg Val Gly Cys Asn Asp Gly Tyr Ser

1878 TCG TGG TAC AGT ATC AAC AAT CCA AAC ACA CAT GTT GGT GCG ATT GTT GGT GGG CCC AAT TCT
 424,Ser Trp Tyr Ser Ile Asn Asn Pro Asn Thr His Val Gly Ala Ile Val Gly Gly Pro Asn Ser

1947 GGG GAT CAA TTT GTT GAC TCG AGA TCA GAT TAC TCT CAT TCT GAA CCC ACG ACT TAT ATG AAT GCA GCA
 447,Gly Asp Gln Phe Val Asp Ser Arg Ser Asp Tyr Ser His Ser Glu Pro Thr Thr Tyr Met Asn Ala Ala

2016 TTT GTA GGA TCC GTA GCC GCT TTG ATT GGT CAA AAT AGA AGG CAA ATT AAT TCA CAA TTT AAC GAA CCA
 470,Phe Val Gly Ser Val Ala Leu Ile Gly Gln Asn Arg Arg Gln Ile Asn Ser Gln Phe Asn Glu Pro

2085 ATT TTA TGT GAT AAA CAA ATT AGC AAG ACG AAG AAT GTT TCA CAG TAA A AAATTGAATATCTATAGTCAGAAATAAATA
 493,Ile Leu Cys Asp Lys Gln Ile Ser Lys Thr Lys Asn Val Ser Gln ***

2161 TATCTACATATAATGTTTACTGTATGGTACATATAATGTATAATCATCCTACAGGCTCATAATTCAATAAAATCATTACTTATGCCTTCGATT
```

Cellulase Inhibited Pepper Greenhouse Trial III
Disease Severity Ratings after Inoculation with *Alternaria alternata*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2254 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 609..2129

(xi) SEQUENCE DESCRIPTION: SEQ ID NO:1:

```
GAATTCAAAT TATGTTAAGA GTTTGTGGAG TCTACATCAT AAACCTGAAT TATGCCTATA      60

TGAATTATGC CTATATAAAG GGGGGGGGGG GCAAATCAAA AAGTATTCAT AAAGAGATCA     120
```

-continued

```
AAACTCTCTC ATCTTGATAA TCATATATAC ACAAACCCTC TCTCCTTTTA TGGAGATCAA      180

ATCCAAATAG TCTTACTTTC GAGAAATAAC GGCCGGAAAA TTCATATCAA ATCCTAATAT      240

ACCTACATTT GAAAAATACG CTACTGACGA TCCTCGAATT ACGGAGAAAT TTATATCAAA      300

TTCAAATATT CCTACGTTCA AAAAATACAC TATTGACGGC CCTCGAATTA TGAAGAAAAT     360

CAAGAGAGAA ACTGATTTAT GTCCATATTG TTTATCAATA AAAAATTATG TTTTTTTCAT      420

ATTTTAATTT GTGATTGCAA TTTATTATTG TGTAAAAAAA TTGTGGGAAA CAAAAATCTC      480

TAATAGGCAA TAGCTCACAT GCCCTATAAA TACCACCATA ACATTATCAA ACTTTCTAAC      540

ATATAGACAT AAATATTAAA TAGTCATAAA CCATATATGT TATATAATAT AATATAATAT      600
```

```
ATATAATA ATG GCT TGT TCA ACG AAT ATT TGG GTT GTT ATA TTC TTC TTG              650
         Met Ala Cys Ser Thr Asn Ile Trp Val Val Ile Phe Phe Leu
          1               5                  10

TGC TTA TTA GCT CGT CCA ATT ATT GCT CAA GAT TAT AAA GAT GCA CTT              698
Cys Leu Leu Ala Arg Pro Ile Ile Ala Gln Asp Tyr Lys Asp Ala Leu
 15              20                  25                  30

GGC AAA TCT ATT TTA TTT TTT GAA GGA CAA CGT TCT GGG AGA CTG CCA              746
Gly Lys Ser Ile Leu Phe Phe Glu Gly Gln Arg Ser Gly Arg Leu Pro
                 35                  40                  45

GTA TCT CAA AGA GTC AAA TGG AGA GGA GAT TCT GCA CTC ATT GAT GGC              794
Val Ser Gln Arg Val Lys Trp Arg Gly Asp Ser Ala Leu Ile Asp Gly
             50                  55                  60

AAA ATT GAA CAT GTG AAC TTA ATT GGC GGG TAC TAT GAT GCT GGT GAC              842
Lys Ile Glu His Val Asn Leu Ile Gly Gly Tyr Tyr Asp Ala Gly Asp
         65                  70                  75

AAC GTG AAA TTT GGA TGG CCC ATG GCT TTT TCT TTA ACT TTA TTG AGT              890
Asn Val Lys Phe Gly Trp Pro Met Ala Phe Ser Leu Thr Leu Leu Ser
     80                  85                  90

TGG GCT GCT ATT GAA TAC CCA ACA CAA ATC TCT TCT GCA AAC CAA CTT              938
Trp Ala Ala Ile Glu Tyr Pro Thr Gln Ile Ser Ser Ala Asn Gln Leu
 95                 100                 105                 110

CCC CAC CTC CAA CGT GCA ATT CGA TGG GGC ACA AAT TTC TTA ATT CGA              986
Pro His Leu Gln Arg Ala Ile Arg Trp Gly Thr Asn Phe Leu Ile Arg
                115                 120                 125

GCC CAT ACT TCA ACT ACC ACT CTC TAT ACT CAG GTT CGA GAT CGA AAT             1034
Ala His Thr Ser Thr Thr Thr Leu Tyr Thr Gln Val Arg Asp Arg Asn
            130                 135                 140

GCA GAT CAC CAA TGT TGG GAG AGA CCA GAA GAC ATG GAT ACA CCA AGA             1082
Ala Asp His Gln Cys Trp Glu Arg Pro Glu Asp Met Asp Thr Pro Arg
        145                 150                 155

ACA TTA TAT AAA ATC ACA TCA AAT TCT CCA GGT TCT GAG GTT GCA GCT             1130
Thr Leu Tyr Lys Ile Thr Ser Asn Ser Pro Gly Ser Glu Val Ala Ala
    160                 165                 170

GAA GTA GCT GCT GCT TTT GCT GCT GCG TCT ATT GTT TTC AAA AAT ATT             1178
Glu Val Ala Ala Ala Phe Ala Ala Ala Ser Ile Val Phe Lys Asn Ile
175                 180                 185                 190

GAT TCC AAT TAC TCT GGT AAA TTA TTA AGA AGA TCC CAA TCT CTA TTT             1226
Asp Ser Asn Tyr Ser Gly Lys Leu Leu Arg Arg Ser Gln Ser Leu Phe
                195                 200                 205

GCA TTT GCG GAC AAG TAT AGA GGA TCT TAC CAG GCT TCT TGC CCA TTC             1274
Ala Phe Ala Asp Lys Tyr Arg Gly Ser Tyr Gln Ala Ser Cys Pro Phe
            210                 215                 220

TAC TGC TCT TAC TCA GGT TAT CAG GAT GAA TTG TTG TGG GCT GCT GCA             1322
Tyr Cys Ser Tyr Ser Gly Tyr Gln Asp Glu Leu Leu Trp Ala Ala Ala
        225                 230                 235

TGG CTA TAC AAG GCA GGT GGA GGA AAC AAT TAT TTA AAC TAT GCT TTA             1370
Trp Leu Tyr Lys Ala Gly Gly Gly Asn Asn Tyr Leu Asn Tyr Ala Leu
    240                 245                 250
```

-continued

```
AAT AAC CAA GGG TGG AGT CAA TGT CCC TCT GAA TTC AGT TGG GAT AAC      1418
Asn Asn Gln Gly Trp Ser Gln Cys Pro Ser Glu Phe Ser Trp Asp Asn
255                 260                 265                 270

AAG TTT GCT GGA GCC CAA ATT TTA CTA GCC AAG GAG TTT CTT AAT GGG      1466
Lys Phe Ala Gly Ala Gln Ile Leu Leu Ala Lys Glu Phe Leu Asn Gly
                275                 280                 285

AAG AGC AAT CTG GAA AAG TTC AAG AAA GAT GCT GAT TCA TTT GTT TGT      1514
Lys Ser Asn Leu Glu Lys Phe Lys Lys Asp Ala Asp Ser Phe Val Cys
            290                 295                 300

GCA TTA ATG CCA GGA AGT AGC TCT GTA CAG ATT AAG ACA ACC CCG GGT      1562
Ala Leu Met Pro Gly Ser Ser Ser Val Gln Ile Lys Thr Thr Pro Gly
        305                 310                 315

GGA CTA TTG TTT TTT AGA GAT AGT AGC AAT TTG CAA TAT GTG TCT GGT      1610
Gly Leu Leu Phe Phe Arg Asp Ser Ser Asn Leu Gln Tyr Val Ser Gly
    320                 325                 330

GCC ACC ATG GTA CTT TTT ATG TAC TCT AAA GTC CTT GAT GCA GCT GGA      1658
Ala Thr Met Val Leu Phe Met Tyr Ser Lys Val Leu Asp Ala Ala Gly
335                 340                 345                 350

AAA GAG GGA ATT ACA TGT GGA TCT GTT AAT TTT TCC ACC TCC AAG ATT      1706
Lys Glu Gly Ile Thr Cys Gly Ser Val Asn Phe Ser Thr Ser Lys Ile
                355                 360                 365

AAA GCC TTT GCA AAA TCA CAG GTA GAC TAC ATA CTT GGT AAC AAT CCA      1754
Lys Ala Phe Ala Lys Ser Gln Val Asp Tyr Ile Leu Gly Asn Asn Pro
                370                 375                 380

CTT CAA ATG TCA TAC ATG GTT GGA TTT GGC AAC AAA TAC CCA ACA CAA      1802
Leu Gln Met Ser Tyr Met Val Gly Phe Gly Asn Lys Tyr Pro Thr Gln
            385                 390                 395

CTC CAC CAT AGA GCC TCA TCA CTT CTT TCA ATT TAT AAC CAC CCC ACC      1850
Leu His His Arg Ala Ser Ser Leu Leu Ser Ile Tyr Asn His Pro Thr
        400                 405                 410

AGG GTG GGC TGC AAC GAT GGC TAT AGT TCG TGG TAC AGT ATC AAC AAT      1898
Arg Val Gly Cys Asn Asp Gly Tyr Ser Ser Trp Tyr Ser Ile Asn Asn
415                 420                 425                 430

CCA AAC CCC AAC ACA CAT GTT GGT GCG ATT GTT GGT GGG CCC AAT TCT      1946
Pro Asn Pro Asn Thr His Val Gly Ala Ile Val Gly Gly Pro Asn Ser
                435                 440                 445

GGG GAT CAA TTT GTT GAC TCG AGA TCA GAT TAC TCT CAT TCT GAA CCC      1994
Gly Asp Gln Phe Val Asp Ser Arg Ser Asp Tyr Ser His Ser Glu Pro
                450                 455                 460

ACG ACT TAT ATG AAT GCA GCA TTT GTA GGA TCC GTA GCC GCT TTG ATT      2042
Thr Thr Tyr Met Asn Ala Ala Phe Val Gly Ser Val Ala Ala Leu Ile
            465                 470                 475

GGT CAA AAT AGA AGG CAA ATT AAT TCA CAA TTT AAC GAA CCA ATT TTA      2090
Gly Gln Asn Arg Arg Gln Ile Asn Ser Gln Phe Asn Glu Pro Ile Leu
        480                 485                 490

TGT GAT AAA CAA ATT AGC ACG AAG AAT GTT TCA CAG TAAAAAATTG           2136
Cys Asp Lys Gln Ile Ser Thr Lys Asn Val Ser Gln
495                 500                 505

AATATCTATA GTCAGAAATA AATATATCTA CATATAATGT TTTACTGTAT GGTACATATA    2196

ATGTATAATC ATCCTACAGG CTCATAATTC AATAAAATCA TTACTTATGC CTTCGATT     2254
```

(2) INFORMATION FOR SEQ ID NO:2:

(i) SEQUENCE CHARACTERISTICS:
        (A) LENGTH: 506 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Cys Ser Thr Asn Ile Trp Val Val Ile Phe Phe Leu Cys Leu
 1               5                  10                  15

Leu Ala Arg Pro Ile Ile Ala Gln Asp Tyr Lys Asp Ala Leu Gly Lys
            20                  25                  30

Ser Ile Leu Phe Phe Glu Gly Gln Arg Ser Gly Arg Leu Pro Val Ser
        35                  40                  45

Gln Arg Val Lys Trp Arg Gly Asp Ser Ala Leu Ile Asp Gly Lys Ile
 50                  55                  60

Glu His Val Asn Leu Ile Gly Gly Tyr Tyr Asp Ala Gly Asp Asn Val
 65                  70                  75                  80

Lys Phe Gly Trp Pro Met Ala Phe Ser Leu Thr Leu Leu Ser Trp Ala
                85                  90                  95

Ala Ile Glu Tyr Pro Thr Gln Ile Ser Ser Ala Asn Gln Leu Pro His
                100                 105                 110

Leu Gln Arg Ala Ile Arg Trp Gly Thr Asn Phe Leu Ile Arg Ala His
            115                 120                 125

Thr Ser Thr Thr Thr Leu Tyr Thr Gln Val Arg Asp Arg Asn Ala Asp
        130                 135                 140

His Gln Cys Trp Glu Arg Pro Glu Asp Met Asp Thr Pro Arg Thr Leu
145                 150                 155                 160

Tyr Lys Ile Thr Ser Asn Ser Pro Gly Ser Glu Val Ala Ala Glu Val
                165                 170                 175

Ala Ala Ala Phe Ala Ala Ala Ser Ile Val Phe Lys Asn Ile Asp Ser
            180                 185                 190

Asn Tyr Ser Gly Lys Leu Leu Arg Arg Ser Gln Ser Leu Phe Ala Phe
        195                 200                 205

Ala Asp Lys Tyr Arg Gly Ser Tyr Gln Ala Ser Cys Pro Phe Tyr Cys
        210                 215                 220

Ser Tyr Ser Gly Tyr Gln Asp Glu Leu Leu Trp Ala Ala Ala Trp Leu
225                 230                 235                 240

Tyr Lys Ala Gly Gly Gly Asn Asn Tyr Leu Asn Tyr Ala Leu Asn Asn
                245                 250                 255

Gln Gly Trp Ser Gln Cys Pro Ser Glu Phe Ser Trp Asp Asn Lys Phe
            260                 265                 270

Ala Gly Ala Gln Ile Leu Leu Ala Lys Glu Phe Leu Asn Gly Lys Ser
        275                 280                 285

Asn Leu Glu Lys Phe Lys Lys Asp Ala Asp Ser Phe Val Cys Ala Leu
        290                 295                 300

Met Pro Gly Ser Ser Ser Val Gln Ile Lys Thr Thr Pro Gly Gly Leu
305                 310                 315                 320

Leu Phe Phe Arg Asp Ser Ser Asn Leu Gln Tyr Val Ser Gly Ala Thr
                325                 330                 335

Met Val Leu Phe Met Tyr Ser Lys Val Leu Asp Ala Ala Gly Lys Glu
            340                 345                 350

Gly Ile Thr Cys Gly Ser Val Asn Phe Ser Thr Ser Lys Ile Lys Ala
        355                 360                 365

Phe Ala Lys Ser Gln Val Asp Tyr Ile Leu Gly Asn Asn Pro Leu Gln
        370                 375                 380

Met Ser Tyr Met Val Gly Phe Gly Asn Lys Tyr Pro Thr Gln Leu His
385                 390                 395                 400

His Arg Ala Ser Ser Leu Leu Ser Ile Tyr Asn His Pro Thr Arg Val
                405                 410                 415

Gly Cys Asn Asp Gly Tyr Ser Ser Trp Tyr Ser Ile Asn Asn Pro Asn
```

```
             420            425           430
Pro Asn Thr His Val Gly Ala Ile Val Gly Pro Asn Ser Gly Asp
            435            440           445

Gln Phe Val Asp Ser Arg Ser Asp Tyr Ser His Ser Glu Pro Thr Thr
450             455              460

Tyr Met Asn Ala Ala Phe Val Gly Ser Val Ala Ala Leu Ile Gly Gln
465             470              475              480

Asn Arg Arg Gln Ile Asn Ser Gln Phe Asn Glu Pro Ile Leu Cys Asp
                485             490              495

Lys Gln Ile Ser Thr Lys Asn Val Ser Gln
            500             505
```

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TTRTCNCCNG CRTCRTARTA NCCNCC                                  26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TCCATRTCYT CNGGNCGYTC CCARCA                                  26

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ATTCGAGGGC CGTCAATAGT GT                                        22

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCAGCTAATA AGCAC                                                          15

(2) INFORMATION FOR SEQ ID NO:7:

-continued

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATATATATAA CCATGGCTTG                                                20

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

AAATTGAAGA TCTATAGTC                                                 19
```

CAPSICUM HEMICELLULASE POLYNUCLEOTIDES AND POLYPEPTIDES

BACKGROUND OF THE INVENTION

1. Field of the Invention

This invention relates to novel polynucleotide constructs, isolated polynucleotides, plant cells containing said polynucleotides, and plants derived therefrom, wherein the polynucleotide constructs comprise a sequence of a hemicellulase, β-(1,4)-endoglucanase, gene from pepper (*Capsicum annuum*). The invention also provides a method of altering a phenotype of a plant by modulating expression of an endogenous hemicellulase gene. In particular it involves the use of recombinant DNA technology to control hemicellulase expression in plants. The invention also provides a method for producing compositions of pepper hemicellulase, cells capable of expressing pepper hemicellulase, and compositions thereof.

2. Description of the Prior Art

Plant development is a complex physiological and biochemical process which involves the coordinated expression of many genes. Ripening, the final phase of fruit development, involves a number of metabolic changes in fruit tissue. These metabolic changes can result from alterations in expression of various genes; the alterations can involve transcriptional and/or post-transcriptional control (e.g., RNA stability, translation, etc.).

An important aspect of the ripening process is fruit softening, which occurs in conjunction with modifications of the cell wall of cells in the fruiting body. Many subtle changes in metabolic activity are involved in this response, and the process of ripening and its control remain incompletely characterized.

For many years, scientists have sought to understand better the process of ripening and to eventually develop methods and plant varieties which were amenable to manipulation of the ripening process. Control of fruit ripening would permit industry to employ more convenient handling, storage, and shipping methods, and ensure that consumers were provided with fruit of suitable ripeness while minimizing wastage resulting from damaged or overripe fruit.

Various types of fruiting plants have been investigated to delineate the genes which control ripening in each plant variety. Several enzymes have been implicated in the ripening process in some plants, however different genes or sets of genes may be causally involved in ripening in different plant varieties.

The prior art discloses ripening-impaired mutants, such as the *rin* mutant which have been used to study fruit ripening. Tigchelaar *Hortic. Sci.* 13: 508 (1978). The use of these mutants to specifically control fruit softening has met with limited success, however, because of the pleiotropic nature of these mutations.

Methods for controlling the expression of certain plant genes can be used to modify a plant's phenotype as desired, such as controlling the rate or time at which fruit ripening occurs. One way to control expression of endogenous plant genes is the inhibition of specific gene expression by antisense suppression (U.S. Pat. Nos. 5,457,281, 5,453,566, 5,365,015, 5,254,800, 5,107,065, and 5,073,676). An alternative method to inhibit expression of specific genes is sense suppression (U.S. Pat. Nos. 5,283,184, 5,231,020, and 5,034,323).

An increase in the activity of polygalacturonase, an enzyme responsible for the degradation of pectin, has been correlated with fruit softening. Recombinant constructs have been prepared containing a plant promoter linked to polygalacturonase cDNA in the antisense direction. These constructs have been inserted into tomato to inhibit the activity of this enzyme in ripening fruit. (Smith et al. (1988) *Nature* 334: 724; Sheehy et al. (1988) *Proc. Nat. Acad. Sci.* 85: 8805; Hiatt et al., U.S. Pat. Nos. 4,801,340, 5,387,757, and 5,457,281; Bridges et al., EPO Publication No. 271,988. U.S. Pat. No. 5,304,490 discusses DNA constructs which contain various genes believed to be involved in the process of fruit ripening. U.S. Pat. No. 5,438,152 discloses methods and compositions for controlling pigment, blossom and scar size, and disease resistance in plants.

Endo-β-1,4-glucanase

Endo-1,4-β-glucanase is an enzyme thought to be involved in fruit softening. It is known to preferentially degrade β-1,4-glycans (e.g., xyloglucan), and is often referred to as a hemicellulase. Hatfield and Nevins, Plant and Cell Physiol. (1986) 27: 541. During ripening, both pectic and hemicellulosic components of fruit cell walls are extensively modified. The involvement of endo-β-1,4-glucanases (EGases; β [1,4] 4-glucan hydrolase; EC3.2.1.4; "hemicellulase") in hemicellulose degradation during vegetative growth and fruit ripening has been implicated (Hayashi et al. (1984) *Plant Physiol.* 75: 605). The presence of hemicellulase activity in ripening tomato fruit and in abscissing tomato flowers has been reported (Roberts et al. (1984) *Planta* 160: 159; Tucker et al. (1984) *Planta* 160: 164). A hemicellulase activity been implicated in cell wall dissolution in bean abscission zones (Tucker and Milligan (*1991*) *Plant Physiol.* 95: 928) and in avocado fruit (Cass et al. (1990) *Mol. Gen. Genet.* 223: 76).

cDNAs and genes encoding endo-1,4-β-glucanase activities have been cloned from avocado (Christoffersen et al. (1984) *Plant Molec. Biol.* 3: 385) and bean (Tucker et al. (1988) *Plant Physiol.* 88: 1257). U.S. Pat. No. 5,328,999 reports a tomato endo-1,4-β-glucanase cDNA and its use for antisense expression to reduce the activity of the gene during fruit ripening in tomato plants harboring the antisense expression construct. Lashbrook et al. (1994) *The Plant Cell* 6: 1485 reports two structurally divergent cDNAs cloned from tomato which may encode proteins having endo-1,4-β-glucanase activity, and reports that the tomato genome has at least four divergent genes which encode proteins having potential hemicellulase activity. U.S. Pat. No. 5,168,064 relates to the use of an endo-1,4-β-glucanase gene in plants. Taylor et al. (1994) *Plant Mol Biol.* 24: 961 reports a cDNA encoding a hemicellulase from the common elder (*Sambucus niger*) which is implicated in leaflet abscission. Yun et al. (1993) *Plant Physiol.* 103: 295, reports the sequence of a hemicellulase cDNA from oat. Lai et al. (1993) *Plant Mol. Biol.* 22: 847, reports the sequence of a cDNA of hemicellulase isolated from germinated wheat. de Silva et al. (1993) *Plant J.* 3: 701 report DNA sequence analysis of a hemicellulase cDNA obtained from nasturium seeds. Slakeski et al. (*1990*) *Mol. Gen. Genet.* 224: 437 report two genes encoding [1,3], hemicellulase in barley. Hoj and Fincher (1995) *Plant J.* 7: 367, discuss possible evolutionary relationships between plant endo-β-1,3-glucanases and endo-β-1,4-glucanases, based on sequence divergence and structural relationships.

Although the various methods described above for attempting to control the process of fruit ripening in various plant varieties have been reported, there exists a need for additional methods for altering fruit ripening in plants, particularly in plant varieties which yield edible fruit, such as peppers and related plant species. The present invention meets these and other needs.

All publications, patents, and patent applications cited herein are incorporated by reference to the same extent as if each individual publication or patent application was specifically and individually stated to be incorporated by reference.

SUMMARY OF THE INVENTION

The present invention generally relates to novel polynucleotide sequences based on the gene encoding endo-1, 4-β-glucanase in pepper (e.g., genus Capsicum). Although described in relation to pepper, the polynucleotide sequences and methods employing them can be used in conjunction with other plant types which naturally express a structurally related endo-1,4-β-glucanase ("hemicellulase") as a component of fruit ripening. By way of example, pepper (in the context of suppression) and tomato (in the context of overexpression) can be suitable candidate hosts for polynucelotide constructs comprising the described Capsicum hemicellulase sequences or variants thereof.

Polynucleotide sequences which comprise a sequence of at least 25 nucleotides which is substantially identical to a cDNA or genomic gene encoding Capsicum hemicellulase polypeptide are provided. The characteristics of the cloned sequences are given, including the nucleotide and predicted amino acid sequences of Capsicum hemicellulase in FIG. 1 (SEQ ID NO:1 and SEQ ID NO:2). Polynucleotides comprising these sequences have a variety of uses. The polynucleotides can serve as templates for the recombinant expression of quantities of Capsicum hemicellulase polypeptides and variants thereof, such as muteins and the like. Polynucleotides comprising these sequences can also serve as sense suppression constructs which can be introduced into a plant genome, such as pepper (Capsicum) or a sufficiently closely related genus and effect inhibition of expression of an endogenous hemicellulase gene thereby delaying or inhibiting the process of fruit ripening, and can also be used for expression or overexpression in tomato (e.g., to increase solids content). Polynucleotides comprising these sequences can also serve as antisense constructs which can be introduced into a plant genome, such as a pepper (e.g., Capsicum) or sufficiently closely related genus and effect inhibition of expression an endogenous hemicellulase gene thereby delaying or inhibiting the process of fruit ripening. Polynucleotides comprising these sequences can also serve as probes for nucleic acid hybridization to detect the transcription rate and mRNA abundance of hemicellulase mRNA in individual plant cells and tissues (or to perform cell typing of tissues in a fruiting body) by in situ hybridization, and in specific cell populations by Northern blot analysis and/or by in situ hybridization (Alwine et al.(1977) *Proc. Natl. Acad. Sci. U.S.A.* 74: 5350) and/or PCR amplification and/or LCR detection. Such recombinant polypeptides and nucleic acid hybridization probes have utility for in vitro diagnostic methods for identification of genome instability, for diagnostic tracking of closly linked genes (e.g., a haplotype linked to an endogenous or inserted hemicellulase gene) during or following conventional crossbreeding, among other uses apparent to those of skill in the art.

In one aspect, the invention provides Capsicum hemicellulase polypeptides and compositions thereof. In one embodiment, Capsicum hemicellulase polypeptides comprise polypeptide sequences which are substantially identical to a sequence shown in FIG. 1. An example of a Capsicum hemicellulase polypeptide is the 507 amino acid long polypeptide shown in FIG. 1 and denoted SEQ ID NO: 2. Also provided are Capsicum hemicellulase polypeptides having detectable endo-1,4-β-glucanse activity, such as the Capsicum hemicellulase polypeptide sequence shown in FIG. 1 as SEQ ID NO: 2 and substantially identical polypeptides. Muteins, fragments, and other structural variants, polymorphic sequence alleles, including naturally-occurring allelic variants are also encompassed in the invention.

In another aspect, the invention relates to methods of reducing fruit softening and inhibiting the degradation of cell wall polymers comprising introducing into a plant an expression cassette having a plant promoter sequence operably linked to a DNA subsequence of at least 25 base pairs substantially identical or substantially complementary to a Capsicum hemicellulase such as shown in FIG. 1 and denoted SEQ ID NO: 1; the DNA subsequence being linked to the promoter sequence either in the opposite orientation for expression (i.e., in the antisense direction) or in the sense orientation as occurs in a naturally occuring Capsicum hemicellulase gene (e.g., for sense suppression), or as a tandem array in both orientations, or variations thereof, including separate antisense and sense constructs introduced into the same plant genome. Preferably, the DNA subsequence is identical to at least 25 nucleotides of the Capsicum hemicellulase sequence. The promoter can be either inducible or constitutive, and may be tissue-specific (e.g., fruiting body only) or development stage-specific, if desired. One example of an inducible promoter is the promoter of the tomato E8 gene. One example of a constitutive promoter is the 35S promoter of cauliflower mosaic virus. A variety of organ-specific plant promoter sequences can be used, such as those disclosed in U.S. Pat. No. 5,391,725, and others known in the art.

The invention also provides antisense polynucleotides expressed in a plant cell. Said antisense polynucleotides are substantially complementary to polynucleotides encoding polypeptide sequences, typically complementary to polynucleotide sequences which are substantially identical to a naturally-occurring Capsicum hemicellulase gene sequence. Such antisense polynucleotides are employed to inhibit transcription and/or RNA processing or stability and/or translation of the hemicellulase mRNA species and thereby effect a reduction in the amount of the respective hemicellulase polypeptide in a cell (e.g., a cell of a plant fruiting body). The antisense polynucleotides can inhibit ripening and tissue softening in susceptible cells (e.g., cell types which express hemicellulase activity for ripening). The antisense polynucleotides are substantially identical to at least 25 contiguous nucleotides of the complementary sequence of the Capsicum hemicellulase cDNA sequence shown in FIG. 1 and denoted SEQ ID NO: 1.

The method can be modified by using an expression cassette as described above plus a second expression cassette having a plant promoter sequence operably linked to a subsequence of at least 25 base pairs derived from a gene encoding a second protein (other than Capsicum hemicellulase) which increases the rate or extent of fruit ripening or fruit tissue softening. The other DNA sequences can be linked to the promoter sequence in the normal orientation (i.e., orientation found in naturally occurring gene) for sense suppression or in the opposite orientation for expression af antisense. Plants suitable for the method include, but are not limited to, tomato and pepper. The expression cassette(s) can be introduced into the plant by any suitable technique for introduction of genetic material into a plant genome. The expression cassette(s) can also be introduced into the plant by a sexual cross.

The present invention also provides a method of inhibiting the activity of an endo-1,4-β-glucanase comprising, introducing into a plant an expression cassette having a plant promoter sequence operably linked to a DNA subsequence of at least 25 base pairs substantially identical to, preferably identical to, a DNA sequence of Capsicum hemicellulase, such as that shown in FIG. 1 and referred to as SEQ ID No: 1; the DNA subsequence is linked to the promoter sequence in either the normal or opposite orientation for expression. Transcription of the expression cassette results in substantial inhibition of endogenous hemicellulase, thereby inhibiting cell wall polysaccharide degradation. In a preferred aspect, the DNA subsequence is linked to the promoter sequence in the normal (sense) orientation suitable for sense suppression of a ripening phenotype.

A plant, preferably pepper, is also provided that contains an expression cassette having a plant promoter sequence operably linked to a DNA subsequence substantially identical, preferably identical, to at least 25 base pairs derived from a DNA sequence encoding a Capsicum hemicellulase, such as that shown in FIG. 1 and referred to as SEQ ID No. 1; the DNA subsequence is linked to the promoter sequence in either the normal or opposite orientation for expression. In a preferred aspect, the DNA subsequence is linked to the promoter sequence in the normal (sense) orientation suitable for sense suppression of a ripening phenotype.

In a preferred embodiment the DNA sequence is a partial or complete Capsicum hemicellulase gene. DNA or RNA equivalents are introduced into plants in a way to produce more of the endogenous transcript, but not to produce an anti-sense transcript. This is preferably accomplished by using a DNA segment (natural or constructed) in which the promoter is positioned in the normal orientation at the 5' end of the encoding region so that a "sense" transcript (rather than antisense transcript) will be produced. The plant cells can be transformed with a variety of vectors, such as viral vectors, episomal vectors, shuttle vectors, Ti plasmid vectors and the like, all in accordance with well known procedures.

The invention still further embraces changing the phenotype of edible fruits, vegetables, roots, foliage and seeds wherein the phenotype results entirely or in part from expression of an endogenous hemicellulase gene. In an embodiment, an introduced polynucleotide encodes a transcript with sequence similarity (i.e., substantial identity) to an endogenous gene (e.g. a endo-1,4-β-glucanase gene) that affects ripening of fruits such as, e.g., pepper fruits or related species fruits. The introduced gene directs transcription of RNA having regions substantially identical to a sequence of least 25 nucleotides of FIG. 1 (SEQ ID NO: 1), and causes suppression of endogenous hemicellulase mRNA levels. Transgenotes with suppressed levels of target gene products will have delayed or changed ripening schedules relative to wild-type plants. Traits of pepper and other fruit and of other edible plant parts associated with the ripening process include sweetness, flavor and aroma, firmness or liquidity, and skin strength and quality.

In an embodiment, an introduced polynucleotide encodes a transcript which encodes an endo-1,4-β-glucanase that affects solids content of, e.g., tomatoes. The introduced gene directs transcription of RNA having regions substantially identical to a sequence of least 25 nucleotides of FIG. 1 (SEQ ID NO. 1), and which produces overexpression of hemicellulase activity in the tomato so as to result in increase solids content. Transgenotes with overexpressed levels of hemicellulase will have increased solids content relative to wild-type plants.

In an embodiment, the invention provides an expression polynucleotide which comprises a promoter sequence operably linked to a first polynucleotide sequence encoding a signal peptide from a Capsicum hemicellulase; the first polynucleotide sequence being joined to a second polynucleotide sequence other than a sequence encoding a full-length Capsicum hemicellulase protein, and preferably the first polynucleotide sequence is joined to a second polynucleotide sequence which encodes less than about three consecutive amino acids, usually no amino acid sequence, of a Capsicum hemicellulase protein immediately adjacent to the signal peptide. Often, the second polynucleotide sequence linked to the first polynucleotide sequence encoding a signal peptide from a Capsicum hemicellulase encodes a protein which is metabolically active in a plant and/or which produces a detectable signal (e.g., green fluorescent protein, luciferase, β-galactosidase, etc.).

In an embodiment, the invention provides an expression polynucleotide which comprises a promoter sequence operably linked to a first polynucleotide sequence encoding at least 12 consecutive amino acids of a Capsicum hemicellulase; the first polynucleotide sequence being joined in reading frame to a second polynucleotide sequence encoding a polypeptide other than a Capsicum hemicellulase protein, thereby jointly encoding a fusion protein. Preferably, the encoded fusion polypeptide is at least 30 amino acids long, and generally less than 10,000 amino acids long. In an aspect, the first polynucleotide sequence encodes an enzymatically active portion of Capsicum hemicellulase. In an aspect, the second polynucleotide sequence encodes an enzymatically active portion of a second protein which can catalytically degrade plant or fungal biomaterials (e.g., ligninase) or a polypeptide portion which enhances the stability of the fusion protein and/or enhances its solubility in a solvent or detergent solution.

A further embodiment involves a polynucleotide (e.g., a DNA isolate) consisting essentially of a genomic DNA sequence encoding Capsicum hemicellulase and more particularly a composition consisting of cDNA molecules which encode the Capsicum hemicellulase protein or a portion of at least 25 amino acids thereof.

In addition to polynucleotides which are substantially identical to all or a portion of a naturally-occurring Capsicum hemicellulase gene or mRNA, the invention provides polynucleotides encoding a Capsicum hemicellulase polypeptide. Such polynucleotides are provided with reference to the novel deduced polypeptide sequence information provided in FIG. 1; SEQ ID NO: 2. Polynucleotides encoding Capsicum hemicellulase polypeptides can be constructed by those skilled in the art on the basis of the disclosed FIG. 1; SEQ ID NO: 2 in view of the degeneracy of the genetic code. In an embodiment, the Capsicum hemicellulase polynucleotides encode a full-length Capsicum hemicellulase polypeptide of SEQ ID NO: 2. In an embodiment, the Capsicum hemicellulase polynucleotides encode a mutein or analog of Capsicum hemicellulase. Capsicum hemicellulase polynucleotides can also encode fragments of a Capsicum hemicellulase polypeptide, and/or fusion proteins comprising a full-length Capsicum hemicellulase polypeptide or fragment or analog thereof in polypeptide linkage to a heterologous polypeptide (e.g., epitope tag, β-galactosidase, chitinase, glutathione-S-transferase, ligninase, cellulase, and the like).

The invention also provides methods for producing a substantially purified Capsicum hemicellulase, such as the hemicellulase protein disclosed in FIG. 1; SEQ ID NO:2, or mutein variants thereof which are substantially identical, preferably at least 85 percent identical. Such methods typically comprise expressing in a host cell a heterologous polynucleotide consisting of (1) a polynucleotide sequence encoding Capsicum hemicellulase operably linked to (2) a heterologous transcription regulatory region (e.g., promoter) capable of driving transcription of the linked Capsicum hemicellulase sequence in the host cell to produce a mRNA which can be translated in the host cell into a Capsicum hemicellulase polypeptide, preferably having hemicellulase activity. Typically, transcription control sequences in the heterologous polynucleotide include transcription termination sequences, polyadenylation sequences, and the like. The heterologous polynucleotide will also include sequences such that the transcribed RNA has a suitable ribosome binding site and untranslated sequences to ensure efficient translation in the host cell; as the host cell may be selected to be prokaryotic (e.g., *E. coli*) or eukaryotic (e.g., higher plant cell, pepper, totato, etc.), the practitioner will select compatible transcription and translation control sequences appropriate for use in the selected host cell. In an embodiment, the Capsicum hemicellulase polypeptide expressed is in polypeptide linkage to a signal sequence, either a naturally-occurring hemicellulase signal peptide or a heterologous signal peptide to effect compartmentalization and/or secretion from the host cell.

The invention also provides a method for producing substantially pure Capsicum hemicellulase polypeptide having detectable hemicellulase activity; the method comprises expressing a Capsicum hemicellulase polynucleotide in a host cell under transcriptional control of a heterologous promoter whereby Capsicum hemicellulase polypeptide is expressed and collected in substantially purified form.

In an embodiment, the invention provides a cell comprising a polynucleotide encoding a Capsicum hemicellulase polypeptide having hemicellulase activity, wherein the cell is capable to express said encoded Capsicum hemicellulase polypeptide under suitable conditions. Such cells may be used for bioremediation, composting, cellulose pulp processing, and other uses. The cell may comprise polynucleotide(s) encoding the expression of additional non-native proteins, such as enzymes (e.g., ligninase) or the like.

The invention also provides Capsicum hemicellulase polynucleotide probes for detection of a hemicellulase mRNA or the hemicellulase gene in nucleic acids obtained from plant cells, or detection of an advantageous hemicellulase allele (e.g., by RFLP or allele-specific PCR analysis) or hemicellulase allele on a linkage group (haplotype) having a desired genotype. Typically, the detection will be by hybridization using a labeled (e.g., $^{32}$P, $^{35}$S, $^{14}$C, $^{3}$H, fluorescent, biotinylated, digoxigeninylated) Capsicum hemicellulase polynucleotide, although Northern blotting, dot blotting, or solution hybridization on bulk RNA or poly A$^+$ RNA isolated from a cell sample may be used, as may PCR amplification using hemicellulase-specific primers.

A further understanding of the nature and advantages of the invention will become apparent by reference to the remaining portions of the specification and drawings.

BRIEF DESCRIPTION OF THE DRAWINGS

FIG. 1 shows the nucleotide (SEQ ID NO:1) and deduced amino acid (SEQ ID NO:2) sequences of a cDNA encoding hemicellulase in *Capsicum annuum*.

DESCRIPTION OF THE PREFERRED EMBODIMENTS

Figure 2:
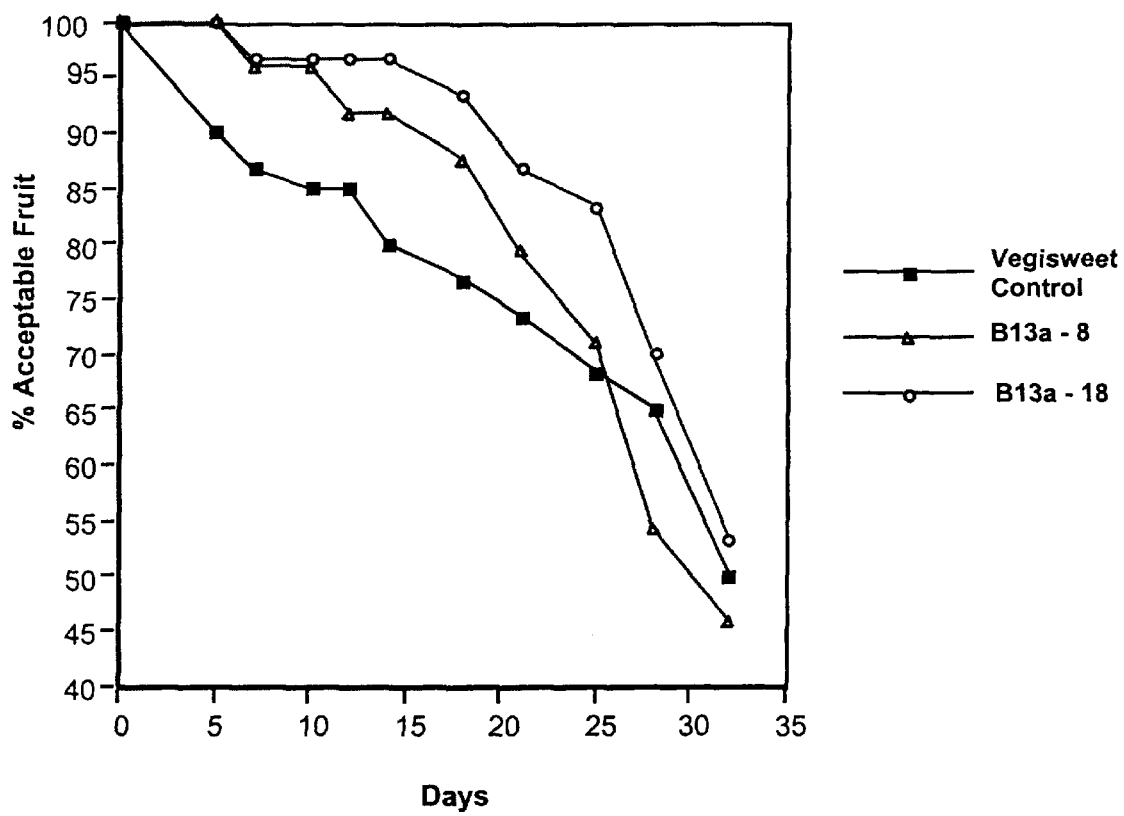
FIG. 2 shows the shelf life decay curves for pepper lines suppressed with a Capsicum hemicellulase suppression transgene (lines B13a-8 and B13a-18) as compared to control (Vegisweet).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a a sample of a wild population or a conventionally used domestic breed, such as would be typical for the species.

As used herein, the term "Capsicum hemicellulase" generally refers to a endo-1,4-β glucanase protein of the Capsicum genus, including isoforms thereof, unless otherwise identified; in its narrowest usage Capsicum hemicellulase refers to a Capsicum hemicellulase polynucleotide and polypeptide sequences having substantial identity to SEQ ID NO: 1 and SEQ ID NO: 2, respectively, or is at least 85 percent substantially identical to SEQ ID NO: 1 or SEQ ID NO: 2, or is at least 89–95 percent substantially identical to SEQ ID NO: 1 or SEQ ID NO: 2. The term Capsicum hemicellulase can also refer to to fragments, analogs, and muteins.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1, or may comprise a complete cDNA or gene sequence. Generally, a reference sequence is at least 20 nucleotides in length, frequently at least 25 nucleotides in length, and often at least 50 nucleotides in length, typically at least 100 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 25 contiguous nucleotide positions wherein a polynucleotide sequence may be compared to a reference sequence of at least 25 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "enhanced comparison window" refers to a window of at least 50 consecutive residues.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 89 to 95 percent sequence identity, more usually at least 99 percent sequence identity as compared to a reference sequence over a comparison window of at least 20 nucleotide positions, frequently over a window of at least 30–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length Capsicum hemicellulase polynucleotide sequence such as shown in FIG. 1 or a segment of a Capsicum hemicellulase protein such as shown in FIG. 1. As used herein the term "substantial identity" excludes any segment of 20 or more nucleotides of the tomato Cel1 gene as shown in U.S. Pat. No. 5,328,999 or Lashbrook et al. (1994) Cell 6: 1485, incorporated herein by reference).

As applied to polypeptides, the term "substantial identity" means that two peptide sequences, when optimally aligned, such as by the programs GAP or BESTFIT using default gap weights, share at least 85 percent sequence identity, preferably at least 89 percent sequence identity, more preferably at least 95 percent sequence identity or more (e.g., 99 percent sequence identity). Preferably, residue positions which are not identical differ by conservative amino acid substitutions. As used herein the term "substantial identity" excludes any segment of 10 or more residues of the tomato Cel1 gene as shown in U.S. Pat. No. 5,328,999 or Lashbrook et al. (1994) Cell 6: 1485, incorporated herein by reference).

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "Capsicum hemicellulase native protein" and "full-length Capsicum hemicellulase protein" as used herein refers to a full-length Capsicum hemicellulase polypeptide of 507 amino acids length consisting of SEQ ID NO: 2 or as naturally occurs in a Capsicum species. A preferred Capsicum Ecase native protein is the polypeptide corresponding to the deduced amino acid sequence shown in FIG. 1 or corresponding to the deduced amino acid sequence of a cognate full-length hemicellulase cDNA of another Capsicum species. Also for example, a native Capsicum hemicellulase protein present in naturally-occurring plant cells which express the Capsicum hemicellulase gene are considered full-length Capsicum hemicellulase proteins.

The term "fragment" as used herein refers to a polypeptide that has an amino-terminal and/or carboxy-terminal deletion, but where the remaining amino acid sequence is identical to the corresponding positions in the sequence deduced from a full-length encoding cDNA sequence (e.g., the cDNA sequence shown in FIG. 1; SEQ ID NO: 2. Fragments typically are at least 14 amino acids long, preferably at least 20 amino acids long, usually at least 50 amino acids long or longer, up to the length of a full-length naturally-occurring Capsicum hemicellulase polypeptide (e.g., about 507 amino acids).

The term "analog", "mutein" or "mutant" as used herein refers to polypeptides which are comprised of a segment of at least 10 amino acids that has substantial identity to a portion of the naturally occurring protein. For example, a Capsicum hemicellulase analog comprises a segment of at least 10 amino acids that has substantial identity to a Capsicum hemicellulase protein, such as the protein of FIG. 1; SEQ ID NO: 2. In an embodiment, a Capsicum hemicellulase analog or mutein has endo-1,4-β glucanase activity under suitable reaction conditions. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring protein. Some analogs may lack biological activity (e.g., endo-1,4-β-glucanase activity) but may still be employed for various uses, including as a competitive inhibitor of an active hemicellulase (i.e., to quench excessive hemicellulase activity in a reaction), or as an oncotic solute, viscosity-enhancing agent, combustible fuel, or foodstuff.

The term "Capsicum hemicellulase polypeptide" is used herein as a generic term to refer to native protein, fragments, or analogs of Capsicum hemicellulase, or such fused to a second polypeptide sequence (e.g., an epitope tag, β-gal, ligninase, or other fusion). Hence, native Capsicum hemicellulase, fragments of Capsicum hemicellulase, and analogs of Capsicum hemicellulase, as well as Capsicum hemicellulase fusion proteins are species of the Capsicum hemicellulase polypeptide genus. Preferred Capsicum hemicellulase polypeptides include: a protein comprising the complete encoded polypeptide sequence shown in FIG. 1 (SEQ ID NO: 2), a polypeptide consisting essentially of the sequence shown in FIG. 1 (SEQ ID NO: 2), including post-translationally modified isoforms. Generally, Capsicum hemicellulase polypeptides are less than 5,000 amino acids long, usually less than 1000 amino acids long, often 507 amino acids long or less.

The term "Capsicum hemicellulase polynucleotide" as used herein refers to a polynucleotide of at least 25 nucleotides wherein the polynucleotide comprises a segment of at least 25 nucleotides which: (1) are at least 85 percent identical to a naturally-occurring Capsicum hemicellulase mRNA sequence or its complement or to a naturally-occurring Capsicum hemicellulase genomic structural gene sequence, and/or (2) encode a Capsicum hemicellulase polypeptide. Due to the degeneracy of the genetic code, some Capsicum hemicellulase polynucleotides encoding a Capsicum hemicellulase polypeptide will be less that 85 percent identical to a naturally-occurring Capsicum hemicellulase polynucleotide. Similarly, some Capsicum hemicellulase polynucleotides which are suitable as hybridization probes, PCR primers, LCR amplimers, and the like will not encode a Capsicum hemicellulase polypeptide.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

A heterologous sequence is one that originates from a foreign species, or, if from the same species, is substantially modified from its original form. As used herein, "heterologous sequence," "exogenous sequence," and "introduced sequence" have the same meaning.

"Operably linked" refers to functional linkage between the affecting sequence (such as a promoter or 3' segments) and the controlled nucleic acid sequence.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein, "plant" refers to either a whole plant, a plant part, a plant cell, or a group of plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

An "isolated" polynucleotide or polypeptide is a polynucleotide or polypeptide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

The term "recombinant" used herein refers to Capsicum hemicellulase polypeptides produced by recombinant DNA techniques wherein the gene coding for protein is cloned by known recombinant DNA technology. For example, the Capsicum hemicellulase gene may be inserted into a suitable DNA vector, such as a bacterial plasmid, and the plasmid used to transform a suitable host. The gene is then optionally expressed in the host to produce the recombinant protein. The transformed host may be prokaryotic or eukaryotic, including plant, mammalian, yeast, Aspergillus and insect cells. One preferred embodiment employs cells as the host. Another preferred embodiment employs plant cells as the host.

Overview

A basis of the present invention is the identification of a unique hemicellulase gene in Capsicum, cloning and isolation of the Capsicum hemicellulase cDNA, determination of the nucleotide and deduced amino acid sequence of Capsicum hemicellulase cDNA, and other aspects of Capsicum hemicellulase which were heretofore unknown and could not be predicted with any degree of certainty.

The present invention provides Capsicum hemicellulase, a hemicellulase involved in fruit ripening, especially in peppers and related plant varieties. The invention provides method for controlling hemicellulase expression and activity in a plant by use of a Capsicum hemicellulase polynucleotide, such as in a sense suppression construct or an antisense construct, or an overexpression construct.

General Methods

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection) and plant cell culture. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., which is incorporated herein by reference) which are provided throughout this document.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications,* eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; *PCR,* eds. McPherson, Quirkes, and Taylor, IRL Press, Oxford; and U.S. Pat. No. 4,683,202, which are incorporated herein by reference).

Capsicum Hemicellulase Polypeptides and Polynucleotides

Cloning of Capsicum Hemicellulase Polynucleotides

Disclosure of the full coding sequences for Capsicum hemicellulase shown in FIG. 1 makes possible the construction of isolated polynucleotides that can direct the expression of Capsicum hemicellulase, fragments thereof, or analogs thereof. Further, the sequence in FIG. 1 makes possible the construction of nucleic acid hybridization probes and PCR primers that can be used to detect RNA and DNA sequences encoding Capsicum ECcase.

Polynucleotides encoding full-length Capsicum hemicellulase or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a Capsicum hemicellulase polypeptide linked downstream (i.e., in translational reading frame orientation; polynucleotide linkage) of a promoter such as the 35S CaMV promoter, the ribulose-1,3-bisphosphate carboxylase small subunit promoter, the phaseolin promoter, the promoter sequence from the E8 gene and other genes in which expression is induced by ethylene, and any other functional plant gene known in the art (e.g., U.S. Pat. Nos. 4,962,028, 5,391,725, and 5,352,605, incorporated herein by reference) which functions in the selected host cell. For example, the isolation and sequence of the E8 promoter is described in detail in Deikman and Fischer (1988) *EMBO J.* 7: 3315, which is incorporated herein by reference. The polynucleotide sequence encoding a Capsicum hemicellulase polypeptide is optionally also linked to an enhancer and a downstream polyadenylation site.

Preferably, these amino acid sequences occur in the given order (in the amino-terminal to carboxy-terminal orientation) and may comprise other intervening and/or terminal sequences; generally such polypeptides are less than 1000 amino acids in length, more usually less than about 500 amino acids in lengths, and frequently approximately 204 amino acids in length. The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Isolated Capsicum hemicellulase polynucleotides typically are less than approximately 10,000 nucleotides in length.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting related hemicellulase RNA or DNA sequences. Polynucleotides of this invention may serve as antisense vectors or sense suppression constructs for introduction into a plant genome or as integrated into a plant genome at a position other than a naturally-occurring hemicellulase locus or in place of a naturally-occurring hemicellulase locus (e.g., by replacement homologous recombination).

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a Capsicum hemicellulase sequence is retained.

Genomic or cDNA clones encoding Capsicum hemicellulase may be isolated from clone libraries using hybridization probes designed on the basis of the nucleotide sequences shown in FIG. 1 and using conventional hybridization screening methods (e.g., Benton W D and Davis R W (1977) *Science* 196: 180; Goodspeed et al. (1989) *Gene* 76: 1; Dunn et al. (1989) *J. Biol. Chem.* 264: 13057). Where a cDNA clone is desired, clone libraries containing cDNA derived from fruiting body cell mRNA or other hemicellulase-expressing cell mRNA are preferred. Alternatively, synthetic polynucleotide sequences corresponding to all or part of the sequences shown in FIG. 1 may be constructed by chemical synthesis of oligonucleotides.

Additionally, polymerase chain reaction (PCR) using primers based on the sequence data disclosed in FIG. 1 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used.

Polynucleotides comprising sequences of approximately at least 30–50 nucleotides, preferably at least 100 nucleotides, corresponding to or complementary to the nucleotide sequence shown in FIG. 1 can serve as PCR primers and/or hybridization probes for identifying and isolating germline genes corresponding to Capsicum hemicellulase. These germline genes may be from a Capsicum species or may be from a related plant variety. Such germline genes may be isolated by various methods conventional in the art, including, but not limited to, by hybridization screening of genomic libraries in bacteriophage λ or cosmid libraries, or by PCR amplification of genomic sequences using primers derived from the sequence shown in FIG. 1. Various plant genomic libraries are publicly available or may be constructed de novo from isolated DNA.

It is apparent to one of skill in the art that nucleotide substitutions, deletions, and additions may be incorporated into the polynucleotides of the invention. Nucleotide sequence variation may result from sequence polymorphisms of various Ecase alleles, minor sequencing errors, and the like. However, such nucleotide substitutions, deletions, and additions should not substantially disrupt the ability of the polynucleotide to hybridize to one of the polynucleotide sequences shown in FIG. 1 (SEQ ID NO:1) under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1 (SEQ ID NO:1), wherein the probe preferentially hybridizes to the specific target such that, for example, a single band corresponding to one or more of the RNA species of Capsicum hemicellulase (or alternatively spliced mRNA species) can be identified on a Northern blot of RNA prepared from a suitable cell source (e.g., a somatic cell of the fruiting body of Capsicum expressing hemicellulase). Polynucleotides of the invention and recombinantly produced Capsicum hemicellulase, and fragments or analogs thereof, may be prepared on the basis of the sequence data provided in FIG. 1 (SEQ ID NO: 1) according to methods known in the art and described in Maniatis et al., *Molecular Cloning: A Laboratory Manual*, 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

Capsicum hemicellulase polynucleotides may be short oligonucleotides (e.g., 20–100 bases long), such as for use as hybridization probes and PCR (or LCR) primers. Capsicum hemicellulase polynucleotide sequences may also comprise part of a larger polynucleotide (e.g., a cloning vector comprising a Capsicum hemicellulase clone) and may be fused, by polynucleotide linkage, in frame with another polynucleotide sequence encoding a different protein (e.g., glutathione S-transferase or β-galactosidase) for encoding expression of a fusion protein. Typically, Capsicum hemicellulase polynucleotides comprise at least 25 consecutive nucleotides which are substantially identical to a naturally-occurring Capsicum hemicellulase sequence (e.g., FIGS. 1, more usually Capsicum hemicellulase polynucleotides comprise at least 50 to 100 consecutive nucleotides which are substantially identical to a naturally-occurring Capsicum hemicellulase sequence, and which are less than 90% identical to a hemicellulase gene from the tomato (U.S. Pat. No. 5,328, 999). However, it will be recognized by those of skill that the minimum length of a Capsicum hemicellulase polynucleotide required for specific hybridization to a Capsicum hemicellulase target sequence will depend on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothiolate, etc.), among others.

Antisense Polynucleotides

Additional embodiments include methods that employ specific antisense polynucleotides complementary to all or part of the sequence shown in FIG. 1 (SEQ ID NO: 1) or a cognate Capsicum Ecase sequence. Such complementary antisense polynucleotides may include nucleotide substitutions, additions, deletions, or transpositions, so long as specific hybridization to the relevant target sequence corresponding to FIG. 1 (SEQ ID NO: 1) is retained as a functional property of the polynucleotide.

Antisense polynucleotides that prevent transcription, alter RNA stability or processing, and/or translation of mRNA corresponding to hemicellulase polypeptides may inhibit ripening and/or tissue softening of fruits, such as peppers and strawberry for example. Antisense polynucleotides of various lengths may be produced, although such antisense polynucleotides typically comprise a sequence of about at least 25 consecutive nucleotides which are substantially identical to a naturally-occurring Capsicum hemicellulase polynucleotide sequence, and typically which are identical to a sequence shown in FIG. 1 (SEQ ID NO:1).

Antisense polynucleotides may be produced from a heterologous expression cassette in a transgenic plant cell (transgenote) used to reconstitute all or part of the adult plant. For general methods relating to antisense polynucleotides, see *Antisense RNA and DNA,* (1988), D. A. Melton, Ed., Cold Spring Harbor Laboratory, Cold Spring Harbor, N.Y.). Antisense constructs such as those described in U.S. Pat. Nos. 5,457,281, 5,387,757, 5,365,015, 5,073, 676 and 5,453,566 can be used with the substitution of the present Capsicum hemicellulase sequence, in antisense orientation, in place the antisense structural gene (e.g., pectin esterase, polygalacturonase, etc.) in the disclosed constructs.

Sense Suppression

U.S. Pat. Nos. 5,283,184, 5,231,020, and 5,034,323 disclose a novel method for altering the phenotype of a plant cell by introducing additional transcription units in sense orientation into the cell. A basis of the present invention is the finding that one or more copies of a Capsicum hemicellulase gene, or portion of the gene, can be transferred into a cell (e.g., pepper or tomato) transcribed in a sense orientation (i.e., produce an RNA transcript which is of the same polarity as that of the RNA transcript encoding the gene product, as in the naturally-occurring gene) and suppress expression of the endogenous hemicellulase (e.g., Cel1) gene in a cell or in cells of an organism, particularly in the fruiting body of a plant. This method is termed "sense suppression". The method utilizes a suppression polynucleotide containing a transcription unit wherein a partial or complete copy of an endogenous hemicellulase gene (e.g., a Capsicum hemicellulase gene) or a homologous gene (i.e., most closely related from another individual, species, genus, order, family, class, or phylum) is operably linked to a promoter such that the suppression polynucleotide (or copies thereof) is transcribed to produce a RNA which is in the same polarity as the mRNA of the endogenous gene (i.e., the polarity which encodes the gene product of the endogenous gene). The suppression polynucleotide is transferred into a cell under conditions where the transferred suppression polynucleotide can be integrated and/or transcribed, wherein transcription of the suppression polynucleotide (or replicated copies thereof) is constitutive and/or under a regulatory control (e.g., inducible, developmentally regulated, hormonally controlled, sex-specific, tissue-specific and the like). Transcription of the suppression polynucleotide inhibits or otherwise suppresses the phenotypic expression of the endogenous gene, by the process of sense suppression. Sense suppression is stable and heritable, but the level or degree of sense suppression can vary between primary transformants (i.e., cells into which the suppression polynucleotide have been transferred by other than inheritance fom a parent cell or organism); thus, it is often desirable to select individuals (cells or organisms) which exhibit the desired level of sense suppression. Such sense-suppressed cells or organisms will have a variety of uses. For example, cells may result in which sense suppression is substantially total, wherein the phenotype normally conferred by the endogenous hemicellulase gene (e.g., ripening and tissue softening) is substantially reduced or extinguished. Sense-suppressed cells may be modulatable where transcription of the suppression polynucleotide is controllable (e.g., inducible promoter and/or enhancer), thereby providing a conditional sense-suppressed cell. Further, partial suppression of phenotype may be accomplished by sense suppression based on the size and degree of similarity of the introduced sequence.

The invention provides plants (cells, cell lines, and multicellular organisms of Kingdom Plantae) which exhibit sense-supression of hemicellulase by a Capsicum hemicellulase expression polynucleotide; such sense-suppression is accomplished by the method of introducing a sense-suppression Capsicum hemicellulase polynucleotide into cells, preferably as an integrated copy, and, with regard to plant organisms, more preferably integrated into the germ-line and capable of heritable transmission to offspring. Thus, the invention provides sense-suppressed cells, sense-suppressed cell lines, sense-suppressed plant organisms, sense-suppressed plant lines propagated by asexual methods (including plant culture), sense-suppressed plant variants propagated by sexual methods, and sense-suppressed cells grafted as tissue to an individual plant.

The invention also provides a method for sense-suppression of a hemicellulase phenotype in a cell or organism, said method comprising the steps of: (1) introducing into the genome of the cell or organism a Capsicum hemicellulase suppression polynucleotide, whereby transcription of the suppression polynucleotide produces a detectable phenotypic change, and (2) determining the detectable phenotypic change.

By way of example, and not limitation, an exemplary preferred embodiment of the present invention entails introducing a partial-length endo-1,4-β-glucanase (hemicellulase) coding sequence in an orientation which would be operably linked to a functional promoter into pepper cells. These transgenotes are grown into plants and variations in ripening and fruit softening are selected. The modified pepper fruit exhibit substantially all of the characteristics of the native plants but exhibit indicia of inhibited ripening and fruit softening.

The ripening process can be manipulated with respect to the quality of the fruit through suppression of hemicellulase genes. The flavor of fruit, such as pepper fruit, is determined predominantly by the relative and absolute concentrations of sugars and acids. The sugar and acid concentrations can be modified by suppressing the expression of genes encoding their biosynthesis or degradation. Assays for the hardness, soluble solids content, sugar, or acid content in fruits of plants transformed with appropriate constructs to suppress parts of the pathway using standard techniques can be conducted in a variety of ways in accordance with the art. The Capsicum hemicellulase gene suppression constructs can also be used to generate plants which have enhanced disease resistance (e.g., to *Alternaria alternata*) and the like.

A broad class of suppressed peppers can be derived from crossing bell pepper with jalapeno and including in the resultant genome at least one copy of a functional Capsicum hemicellulase suppression construct.

Suitable sources for gene sequences, such as plant promoters, usable in accordance with the present invention are e.g., plants, in particular higher plants.

A suitable hemicellulase sense suppression construct comprises a suitable promoter which functions in the selected host plant (e.g., pepper) operably linked to a Capsicum hemicellulase sequence of at least 50 nucleotides which is substantially identical, preferably at least 90 precent identical, often at least 95 percent identical or 100 percent identical to the Capsicum hemicellulase sequence shown in FIG. 1 (SEQ ID NO: 1). It is not necessary for the Capsicum hemicellulase sequence to encode a functional protein, to comprise a translation start codon, ribosome-binding site, termination codon, or polyadenylation tract.

The introduced sequence (hemicellulase sense suppression construct), needing less than absolute sequence identity to FIG. 1 or to the endogenous hemicellulase gene to be inhibited, also need not be full length, relative to either the primary transcription product or fully processed mRNA. In this regard and in accordance with the present invention, transformation of sense suppression constructs having partial or truncated Capsicum hemicellulase structural gene sequences also inhibits expression of the endogenous hemicellulase gene in the host plant.

A higher degree of sequence identity in a shorter than full length sequence compensates for a longer less identical sequence. Furthermore, the introduced sequence need not have the same intron or exon pattern, and homology of non-coding segments will be equally effective. Normally, a sequence of greater than 50–100 nucleotides should be used, though a sequence of greater than about 200–300 nucleotides would be preferred, and a sequence of greater than 500–1000 nucleotides, and may comprise all of the Capsicum hemicellulase cDNA or genomic gene; generally, the sense suppression construct is less than 50,000 nucleotides, often less than 10,000 nucleotides, and usually less than 2500 nucleotides, including promoter.

It should be noted that it is possible to produce the same effect on multiple proteins using a single transformation by fusing multiple sequences together to coordinately repress various different genes in addition to hemicellulase. Assuming a sufficient number of introductions are made, the introduced sequence need not be linked to an operative promoter sequence. However, a promoter sequence would be preferred, particularly a partially or fully constitutive promoter.

Expression of Functional Capsicum Hemicellulase

Whereas expression of an endogenous related hemicellulase gene and/or the encoded protein can be inhibited by sense suppression and/or antisense methods, the invention also provides polynucleotides which encode a Capsicum hemicellulase or variant thereof and which, when introduced into a suitable plant genome, are expressed as enzymatically active hemicellulase protein in the host plant. Such polynucleotides can be used for a variety of purposes, including but not limited to enhancement and/or control of ripening, control of texture (e.g., softness, resilience, viscosity, etc.), control of solids content, control of sugar content, control of acid content, altered timing of ripening, or inducible ripening and fruit body softening, among other related uses.

For expression or overexpression of enzymatically active Capsicum hemicellulase, a polynucleotide encoding a Capsicum hemicellulase polypeptide having detectable hemicellulase activity ($\beta$-[1,4] 4-glucan hydrolase; EC3.2.1.4) is introduced into a suitable plant genome (e.g., pepper, tomato, tomatillo, or other suitable plant variety) in a form suitable for expression as desired. Typically, the Capsicum hemicellulase encoding polynucleotide is operably linked to a transcriptional regulatory sequence (e.g., promoter, optional enhancer, polyadenylation sequence, etc.) capable of driving transcription of the Capsicum hemicellulase encoding sequence such that a translatable mRNA is ultimately produced (i.e., RNA splicing of the primary transcript can be required in some embodiments). In a variation, a Capsicum hemicellulase encoding polynucleotide can be targeted, by homologous recombination gene targeting, into a position adjacent to an operable endogenous promoter in a plant genome, such that the resultant endogenous chromosomal locus comprises a Capsicum hemicellulase encoding polynucleotide in operable linkage to an endogenous promoter, and optionally an endogenous polyadenylation sequence and transcription termination sequence. In an embodiment, the Capsicum hemicellulase encoding polynucleotide can encode a full-length Capsicum hemicellulase protein, although truncated variants or other deletion, addition, or substitution variants of enzymatically active hemicellulase can be used. In an embodiment, the Capsicum hemicellulase encoding polynucleotide encodes a fusion protein comprising a full-length Capsicum hemicellulase protein or enzymatically active portion thereof in polypeptide linkage to a fusion partner sequence, such as the sequence of a naturally-occurring gene other than Capsicum hemicellulase. In one variation, the fusion partner sequence is all or a portion of a hemicellulase protein other than Capsicum hemicellulase. In a variation, a portion of a Capsicum hemicellulase polypeptide which by itself lacks enzymatic activity is linked via polypeptide linkage to a portion of a second (non-Capsicum) hemicellulase protein, whereby the fusion protein has detectable hemicellulase activity.

A Capsicum Ecase encoding polynucleotide typically in operable linkage to a transcriptional regulatory sequence (e.g., promoter) and capable of expression is introduced into a genome of a suitable plant variety (e.g., pepper, tomoato, tomatillo, etc.). Individuals exhibiting a desired phenotype characterized by expression of the Capsicum hemicellulase protein encoded by the introduced polynucleotide are selected on the basis of a desired hemicellulase expression phenotype which is determined, such as by enzyme assay, visual inspection, textural inspection, measurement of soluble solids, crispness, and the like.

Thus, the invention provides a means of expressing a Capsicum hemicellulase under control of a heterologous promoter for any desired purpose. One example of such a use is the expression of a Capsicum hemicellulase protein in a tomato to enhance ripening and tissue softening. It can be advantageous to use Capsicum hemicellulase expression constructs to produce expression of a hyperphysiological level of hemicellulase activity in a plant tissue. For example, plants expressing Capsicum hemicellulase encoded on a polynucleotide of the invention can exhibit substantially higher hemicellulase (hemicellulase) activities than a native plant of the same variety; in some cases the hemicellulase activity can be two to three times higher, or more, than in an a control wild-type plant of the same variety. Such plants exhibiting enhanced levels of hemicellulase activity can possess advantageous properties, such as increased tissue softening, advanced ripening, increased soluble solids, enhanced sugar content, enhanced acidity, and the like.

Tomato plants of use with the invention include cultivated tomato varieties of the genus Lycopersicon in particular, *Lycopersicon esculentum*. This includes fresh market tomato, processing tomato, and cherry tomato. Fresh market tomato varieties of interest include Sunny, Duke, FTE 12, Ace, Bingo, Casino Royale, Jack Pot, Valerie, Sweepstakes, Keno and Olympic and numerous others well known in the art. Additional examples can be found in the "New Vegetable Varieties List" published by the American Seed Trade Association (1990); which is incorporated herein by reference.

Constructs and Introduction

In considering the expected temporal stage of expression of the introduced gene, relevant factors include the type of promoter, the temporal pattern of the promoter, and the operation of the promoter in view of its position within the genome. A promoter which is expressed concurrently with or prior to the normal activation of the homologous endogenous sequence is preferred. A constitutive promoter is most preferred, such as the cauliflower mosaic virus promoter. This promoter is constitutive because its operation is relatively independent of the developmental stage of the cell in which it is contained. A regulated promoter, such as ones associated with the ribulose-1,5-bisphosphate carboxylase, the chlorophyll binding proteins or the glycine-rich root protein genes are also suitable. This control may be either temporal with respect to the developmental stage of the cell, or based upon differential expression by different parts or organs of the plant.

As an example, some genes involved in ripening of fruit (e.g. tomato) are expressed in the fruit only at the time of ripening. In some such cases it will be useful to express the exogenous (introduced) sequence only at the time of ripening. Often this can be accomplished by using a promoter of the endogenous gene (operably linked to the introduced polynucleotide) to control the expression of the exogenous transcript. Other promoters that express at the appropriate time (in this case the time of ripening), both from genes of the target plant species and those of other plant species that are appropriately regulated in the target plant, can be used.

Another way to regulate the time of expression of the introduced sequence is by linking the introduced sequence to an inducible promoter that can be activated by causing the plant (or plant part) to be exposed to a salt, a metal, chemical, UV or other light source, or another activating treatment. It may also be desirable to suppress a gene in one part of a plant only using plant promoters that direct transcription in one part or organ of a plant only (i.e., fruiting body).

As referred to above, the operation of a promoter may vary depending on its location in the genome. Thus, a regulated promoter may operate differently from how it does in its normal location, e.g., it may become fully or partially constitutive.

It is preferred to have the DNA sequence linked to and situated at a distance from the promoter corresponding to the distance at which the promoter is normally most effective so as to ensure sufficient transcriptional activity. This distance should be within about 1000 nucleotides, preferably within about 500 nucleotides and more preferably within about 300 nucleotides of the translation initiation codon.

At the 3' end of the coding sequence, operably linked segments may also be included. Thus, it would be optimum to have a 3' untranslated region containing the polyadenylation site and any relevant transcription termination sites. A 3' sequence of less than about 1000 nucleotides is sufficient, about 500 preferred and about 300, or the length of the 3' untranslated tail of the endogenous sequence is more preferred.

If the introduced Capsicum hemicellulase gene is an intact gene (meaning a complete gene containing coding sequences, intron, promoter, enhancers and other cis-acting regulatory elements either upstream (5') or downstream (3') of the coding sequences), a fraction of independent transgenotes, depending on the gene, may carry the introduced gene in locations that result in abnormal expression, i.e., expression at abnormal times in development. If the introduced gene is a chimeric gene (meaning that one or more elements, such as a promoter, from another gene has been substituted for a component of the intact gene or added to the intact gene, including coding sequences fused to upstream and downstream sequences necessary or beneficial for expression) and is driven by a constitutive (fully or partially) promoter, then abnormal levels and times of expression will be achieved in a large fraction of transgenotes. If the introduced gene is a chimeric gene and is driven by a developmentally regulated promoter, depending on the promoter, some fraction of transgenotes will show abnormal levels and times of expression of the introduced gene. The strength of the promoter or other cis element can be the same, lower, or higher than the coding sequence's usual promoter. The timing in development can be earlier or the same.

The likelihood of obtaining a desirable transgenote will depend upon the number of transgenotes screened and the efficiency of actual transformation and expression of the foreign nucleic acid sequence. Typically, at least about 25 to 50 transgenotes will be screened, but 100 to 500 or more may need to be screened before the described effect is seen.

In general, suppression polynucleotides contain a eukaryotic promoter capable of functioning in the cell into which the suppression polynucleotide is to be transferred. Operably linked to the promoter is a transcribable Capsicum hemicellulase polynucleotide sequence. The transcribable Capsicum hemicellulase polynucleotide sequence is at least 25 nucleotides long, more usually at least 50–100 nucleotides long, frequently at least 100–250 nucleotides long, often at least 500 nucleotides long or longer, up to the length of the complete endogenous gene (spanning promoter through transcription termination sequence/polyadenylation site). The transcribable Capsicum hemicellulase sequence is positioned relative to the promoter such that a RNA transcript of the transcribable sequence is the same polarity as the mRNA transcript of the endogenous gene (i.e., sense orientation). The suppression polynucleotide may be part of a larger polynucleotide, such as a transgene having a selectable marker to identify cells having integrated the transgene, or a homologous recombination construct having selectable marker(s) and homology regions for targeting the suppression polynucleotide to a predetermined location in the genome of cells. Suppression polynucleotides may be in the form of a heterologous expression cassette in a transfectant cell or transgenic cell. Often, the suppression polynucleotide is obtained as a vector produced with DNA isolated from a cloned copy (or portion thereof) of the target endogenous gene to be suppressed. The suppression polynucleotide sequence is usually isolated as part of a genomic gene clone, although in some embodiments a cDNA clone (or portion thereof) of the target gene to be suppressed can be employed (for general cDNA methods see, Goodspeed et al. (1989) Gene 76: 1; Dunn et al. (1989) J. Biol. Chem. 264: 13057).

Vectors containing a suppression polynucleotide are typically grown in E. coli and then isolated using standard molecular biology methods, or may be synthesized as oligonucleotides. Direct polynucleotide synthesis and ligation (if necessary) which does not require prokaryotic or eukaryotic vectors may also be done. Polynucleotides (and transgenes comprising such) can be transferred to host cells by any suitable technique, including microinjection, electroporation, lipofection, biolistics, calcium phosphate precipitation, and viral-based vectors, among others (e.g., U.S. Pat. Nos. 5,442,052, 5,354,854, 5,278,057, 5,262,316, 5,137,817, and 4,962,028, incorporated herein by reference). A preferred method of introducing the nucleic acid segments into plant cells is to infect a plant cell, an explant, a meristem or a seed with *Agrobacterium tumefaciens* transformed with the segment. Under appropriate conditions known in the art, the transformed plant cells are grown to form shoots, roots, and develop further into plants. The nucleic acid segments can be introduced into appropriate plant cells, for example, by means of the Ti plasmid of *Agrobacterium tumefaciens*. The Ti plasmid is transmitted to plant cells upon infection by *Agrobacterium tumefaciens,* and is stably integrated into the plant genome (Horsch et al., (1984) "Inheritance of Functional Foreign Genes in Plants," Science, 233:496–498; Fraley et al., (1983) Proc. Natl. Acad. Sci. USA 80:4803). One Agrobacterium method is in planta Agrobacterium-mediated gene transfer by infiltration, e.g., of adult Arabidopsis thaliana plants; Bechtold et al. (*1993*) C.R. Acad. Sci. Life Sciences 316: 1194 et seq., incorporated herein by reference).

All plant cells which can be transformed by Agrobacterium and whole plants regenerated from the transformed cells can also be transformed according to the invention so as to produce transformed whole plants which contain the transferred foreign nucleic acid sequence.

Plant cells can be transformed with Agrobacterium in various ways, including: co-cultivation of Agrobacterium with cultured isolated protoplasts, transformation of cells or tissues with Agrobacterium, or transformation of seeds, apices or meristems with Agrobacterium.

A preferred system is the binary system in which two plasmids are needed: a T-DNA containing plasmid and a vir plasmid. Any one of a number of T-DNA containing plasmids can be used, the only requirement is that one be able to select independently for each of the two plasmids.

After transformation of the plant cell or plant, those plant cells or plants transformed by the Ti plasmid so that the desired DNA segment is integrated can be selected by an appropriate phenotypic marker. These phenotypic markers include, but are not limited to, antibiotic resistance, herbicide resistance or visual observation. Other phenotypic markers are known in the art and may be used in this invention.

If naked nucleic acid introduction methods are chosen, then the vector need be no more than the minimal nucleic acid sequences necessary to confer the desired traits, without the need for additional other sequences. Thus, the possible vectors include the Ti plasmid vectors, shuttle vectors designed merely to maximally yield high numbers of copies, episomal vectors containing minimal sequences necessary for ultimate replication once transformation has occurred, transposon vectors, homologous recombination vectors, mini-chromosome vectors, and viral vectors, including the possibility of RNA forms of the gene sequences. The selection of vectors and methods to construct them are commonly known to persons of ordinary skill in the art and are described in general technical references (Methods in Enzymology, supra).

However, any additional attached vector sequences which will confer resistance to degradation of the nucleic acid fragment to be introduced, which assists in the process of genomic integration or provides a means to easily select for those cells or plants which are actually, in fact, transformed are advantageous and greatly decrease the difficulty of selecting useable transgenotes.

All transformable plants from which whole regenerated plants can be generated can be used in the present invention. Monocots may be transformed with Agrobacterium by electroporation (Fromm et al. [1986] Nature 319:791–793; Rhodes et al. Science [1988] 240: 204–207); by direct gene transfer (Baker et al. [1985] Plant Genetics 201–211); by using pollen-mediated vectors (EP 0 270 356); and by injection of DNA into floral tillers (de la Pena et al. [1987], Nature 325:274–276).

Regeneration

Normally, regeneration will be involved in obtaining a whole plant from the transformation process. The term "transgenote" refers to the immediate product of the transformation process and to resultant whole transgenic plants.

The term "regeneration" as used herein, means growing a whole plant from a plant cell, a group of plant cells, a plant part or a plant piece (e.g. from a protoplast, callus, or tissue part).

Plant regeneration from cultural protoplasts is described in Evans et al., "Protoplasts Isolation and Culture," *Handbook of Plant Cell Cultures* 1:124–176 (MacMillan Publishing Co. New York 1983); M. R. Davey, "Recent Developments in the Culture and Regeneration of Plant Protoplasts," *Protoplasts*, (1983)—Lecture Proceedings, pp.12–29, (Birkhauser, Basal 1983); P. J. Dale, "Protoplast Culture and Plant Regeneration of Cereals and Other Recalcitrant Crops," *Protoplasts* (1983)—Lecture Proceedings, pp. 31–41, (Birkhauser, Basel 1983); and H. Binding, "Regeneration of Plants," *Plant Protoplasts*, pp.21–73, (CRC Press, Boca Raton 1985).

Regeneration from protoplasts varies from species to species of plants, but generally a suspension of transformed protoplasts containing copies of the exogenous sequence is first made. In certain species embryo formation can then be induced from the protoplast suspension, to the stage of ripening and germination as natural embryos. The culture media will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

Regeneration also occurs from plant callus, explants, organs or parts. Transformation can be performed in the context of organ or plant part regeneration. See, *Methods in Enzymology*, supra; also *Methods in Enzymology*, Vol. 118; and Klee et al., (1987) *Annual Review of Plant Physiology*, 38:467–486.

In vegetatively propagated crops, the mature transgenic plants are propagated by the taking of cuttings or by tissue culture techniques to produce multiple identical plants for trialling, such as testing for production characteristics. Selection of desirable transgenotes is made and new varieties are obtained thereby, and propagated vegetatively for commercial sale.

In seed propagated crops, the mature transgenic plants are self crossed to produce a homozygous inbred plant. The inbred plant produces seed containing the gene for the newly introduced foreign gene activity level. These seeds can be grown to produce plants that would produce the selected phenotype.

The inbreds according to this invention can be used to develop new hybrids. In this method a selected inbred line is crossed with another inbred line to produce the hybrid. The offspring resulting from the first experimental crossing of two parents is known in the art as the F1 hybrid, or first filial generation. Of the two parents crossed to produce F1 progeny according to the present invention, one or both parents can be transgenic plants.

Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

Identification and Selection

Identification and selection (or screening) of transgenotes for further study will typically be based upon an assay for the desired characteristic, such as detemining fruit ripnes, hardness, texture, color, soluble solids, and may involve biochemical assays of either enzyme activity or product quantitation. Identification of transgenetics with a changed hemicellulase phenotype will typically be made by assaying mature plants grown from transgenote cells, or by assaying individual transgenote cells or small clones of such cells. Typically, transgenotes will be grown into plants bearing the fruiting body and the hemicellulase gene activities will be monitored, such as by visual appearance (shape and texture of the fruit) or biochemical assays (hemicellulase assays, Northern blots, or the like. Appropriate plants will be selected and further evaluated.

Production of Capsicum Hemicellulase Polypeptides

The nucleotide and amino acid sequences shown in FIG. 1 (SEQ ID NO:1 and SEQ ID NO:2) enable those of skill in the art to produce polypeptides corresponding to all or part of the full-length Capsicum hemicellulase polypeptide sequences. Such polypeptides may be produced in prokaryotic or eukaryotic host cells by expression of polynucleotides encoding Capsicum hemicellulase, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif.

Although one class of preferred embodiments is fragments having amino- and/or carboxy-termini corresponding to amino acid positions near functional domains borders, alternative Capsicum hemicellulase fragments may be prepared. The choice of the amino- and carboxy-termini of such fragments rests with the discretion of the practitioner and will be made based on experimental considerations such as ease of construction, stability to proteolysis, thermal stability, amino- or carboxyl-terminal residue modification, or other considerations.

The following examples are given to illustrate the invention, but are not to be limiting thereof. All percentages given throughout the specification are based upon weight unless otherwise indicated. All protein molecular weights are based on mean average molecular weights unless otherwise indicated.

EXPERIMENTAL EXAMPLES

In general, preparation of plasmid DNA, restriction enzyme digestion, agarose gel electrophoresis of DNA, Southern blots, DNA ligation and bacterial transformation were carried out using standard methods. (Maniatis et al., *Molecular Cloning, A Laboratory Manual*, Cold Spring Harbor Laboratory (1982), referred to herein as "Maniatis" and hereby incorporated by reference.) Western blots and other standard molecular biology techniques are also described in Ausubel et al., (1987) *Current Protocols in Molecular Biology*, Vols. 1 and 2, and hereby incorporated by reference.

Example 1

Cloning of Pepper Hemicellulase Gene

At least two hemicellulase genes are expressed in tomato (Lashbrook et al. *The Plant Cell* 6: 1485). To determine if pepper, *Capsicum annuum* DNAP VS300-1, had a hemicellulase gene or genes present in the genome and expressed as mRNA, a cDNA library derived from the *Capsicum annuum* fruit was screened using a tomato Cel1 gene and selected oligonucleotides, as described below, as probes.

cDNA and Genomic Library Construction

Double-stranded cDNA was prepared from pepper pericarp (mature red stage) polyA+ mRNA using a commercial cDNA synthesis kit (Amersham), and then ligated to λGT10 arms (Stratagene) and packaged in vitro (Gigapack, Stratagene). Library screening was with random primer-labeled (α-[$^{32}$P] dCTP >400 Ci/mmol, Amersham) full-length tomato Cel1 cDNA (pCL1.8) and kinase-labeled (Chaconas and van de Sande, 1980) degenerate oligonucleotides kindly provided by Dr. A. Bennett (U C Davis). The sequences of the oligonucleotides used for screening were 5'-TT[A/G]TC [A/T/G/C]CC[A/T/G/C]GC[A/G]TC[A/G]TA[A/G]TA[A/T/G/C]CC[A/T/G/C]CC-3' (SEQ ID NO:3) and 5'-TCCAT[A/G]TC[T/C]TC[A/T/G/C]GG[A/T/G/C]CG[T/C]TCCCA[A/G]CA-3' (SEQ ID NO:4). These degenerate oligonucleotides corresponded to regions of sequence conservation in the avocado fruit and bean abscission layer hemicellulases. Reduced stringency hybridization was in 5× SSC, 0.05M NaPO4 pH 6.8, 10× Dehardts, 0.1% (v/v) SDS, 0.1% denatured salmon sperm DNA and 10% (w/v) dextran sulfate at 50° C. for labeled cDNA and 42° C. for the mixed oligonucleotides. Post hybridization washes were 45° C. in 2× SSC for oligonucleotide hybridized filters, and 0.1× SSC for the cDNA hybridized filters.

For construction of a genomic library, a nuclear preparation of pepper leaf genomic DNA (Dooner et al., 1991) was partially digested with Sau3A, size fractionated and ligated to λDASH III (Stratagene). Approximately 600,000 recombinant phage were screened with a pepper PCEL1 riboprobe (see below).

DNA sequencing was conducted by the dideoxy chain-ting method of Sanger et al. (1977) using the Sequenase II kit of US Biochemicals.

RNA Isolation and Expression Analysis

Total RNA was isolated from pepper tissues using a phenol-chloroform extraction method described in Dunsmuir et al. The expression of introduced genes in regenerated plants. In: *Plant Molecular Biology Manual* vol. 9, Gelvin and Schilperoot, eds. (1987) Plenum Press, New York, pp. 45–59. In order to reproducibly extract intact RNA, we find that it is essential to include a high concentration of reducing agent (e.g., 0.1 M DTT) in the homogenization buffer.

RNA electrophoresis for Northern blot analysis was performed according to Sambrook et al (1989) op.cit. Samples were electrophoresed on 1.5% (w/v) agarose 6% (v/v) formaldehyde gels and then blotted onto Duralon-UV filters (Stratagene).

Following prehybridization at 65° C. for 4–5 h in hybridization buffer (7% SDS, 0.25M Na$_2$HPO$_4$, 1 mM EDTA and 1% [w/v] BSA), UV-crosslinked filters were typically hybridized overnight with denatured, random primer-labelled Cell probe using the same conditions. Unless otherwise stated, filters were washed for 1–2 h at 65° C. in 0.1× SSC and 0.1% (w/v) SDS prior to autoradiographic exposure.

RNase protection analysis was performed as described in Jones et al (1985) *EMBO J.* 4: 2411. Radioactive labeled (α-$^{32}$P [400 Ci/mmol; Amersham) antisense probe was generated by in vitro transcription of XbaI linearized, PCEL1 riboprobe vector (pCP35SR) with T3 polymerase (Stratagene). pCP35-SR is a 230 bp SspI-EcoRI fragment of the PCEL1 ORF subcloned into BS+.

Primer extension analysis was performed as described in Harpster et al. (1988) *Mol. Gen. Genet.* 212: 182. Primers for expression analysis and 5' transcription start site mapping are 5'ATTCGAGGGCCGTCAATAGTGT-3' (SEQ ID NO:5) (2.10 kb PCEL1 transcript) and 5'CCAGCTAAT AAGCAC-3' (SEQ ID NO:6) (1.70 kb PCEL1 transcript).

Partial Purification of Cellulase and Activity Measurements

The partial purification of cellulase activity from red pepper pericarp employed methodology described in Awad and Lewis (1980) *J. Food Sci.* 45: 1625 with several modifications. Frozen tissue (40–60 gm) was first ground to a fine powder with liquid N$_2$, after which the powder was extracted extensively with 100% acetone until pigment was no longer evident in the filtrate. Acetone extracted material was dried completely, rehydrated in 15 volumes of homogenization buffer (40 mM NaOAc pH 7.5, 0.4M NaCl, 0.5% [v/v] Triton-X and a proteinase inhibitor cocktail [1 mM PMSF, 0.1 mM leupeptin, 1 mM N-ethyl maleimide, 1 mM benzamidine, 10 mM ε-amino caproic acid and 5 mM phenanthroline) and ground to a fine slurry with two 30s bursts of a Polytron set at high speed. Following centrifugation (5 K rpm for 15 min at 4° C.) in order to remove insolubles, the supernatant was heated to 50° C. for 10 min and centrifuged again (same conditions). The resultant supernatant was adjusted to 80%(v/v) acetone and held at 4° C. for a minimum of 30 min, after which the preparation was again centifuged. The pellet was air dried and resuspended in 15 ml of 40 mM NaOAc pH 7.5 ("column buffer") by Dounce homogenation. After pelleting insolubles, the extract was passed 2× over a 10 ml column of cellulose powder (CF-11, Whatman) equilibrated in 40 mM NaOAc pH 7.5, followed by extensive washing with column buffer. As a final step, the column was washed with elution buffer (0.1 M cellobiose, 0.1 M NaCl and 40 mM NaOAc pH 7.5) and eluted protein concentrated with Centricon-10 filtration units (Amicon) using conditions specified by the manufacturer.

Cellulose activity was routinely measured by incubation of a protein extract with 1 ml of 1.25% (w/v) carboxymethylcellulose (CMC; type 7H3SF [Aqualon; a division of Hercules Inc.]) in 40 mM NaOAc pH 7.5. A subsequent change in the intrinsic viscosity of the sustrate is then measured by recording the retention time of CMC as it gravitationally drips from a graduated pipette. Reactions were performed at room temperature for a minimum of 4 hours (time required for completion of hydrolysis). To calculate relative specific activity, a dilution series of 1 mg/ml commercial cellulase (*Trichoderma viride* Sigma Corp.) is used for making a standard curve in which retention time is plotted as a function of known amounts of crude cellulase protein. Relative units derived from this plot are then divided by the mgs of plant protein extract assayed. Protein concentrations were determined using the dye binding method of Bradford (Bradford, *Anal. Biochem*, 72:248–254, 1976).

Preparation of Protein Extracts and Gel Electrophoresis

For electrophoresis or activity measurements, protein extracts were prepared by grinding tissue to a powder in liquid $N_2$, after which the powder was ground to a slurry in the same homogenization buffer used in the purification of cellulase. Soluble debris was then removed by centrifugation in a microcentrifuge and the supernatant directly measured for activity. To prepare samples for electrophoresis on 10% SDS-PAGE gels (Laemmli, *Nature*, 227:680–685, 1970), supernatants were adjusted to 80% acetone, incubated on ice for a minimum of 30 min, centrifuged for 10 min at 4° C. and the resultant pellets dried and resuspended directly in sample loading buffer.

Antibody Preparation and Western Blot

Rabbit antiserum to pepper cellulase was obtained by inoculation with a Protein A/cell fusion protein. Briefly, an NcoI (partial digest)-PstI fragment lacking sequence for 85 amino acids at the 5' end of the Cel1 gene was gel purified and subcloned into the Protein A fusion protein vector pGMM8. The resultant construct, pGMM8-Cel1L, produces a 78 kD fusion protein comprising one Protein A binding domain at the amino terminus translationally fused to a functionally inactive deletion derivative of the Cel1 gene lacking the putative signal sequence. The overexpressed fusion protein, which occurred predominantly in inclusion bodies, was then solubilized by resuspension of pelleted inclusion bodies in gel loading buffer. Protein samples were then boiled and electrophoresed on 3 mm thick, 10% SDS-PAGE preparative gels, after which the gel was lightly stained with Coomassie to reveal the correct band. Slices of acrylamide containing the fusion protein were then provided to BABCO (Richmond, Calif.), for antibody production.

Immunoblotting of protein extracts was carried out as described in Lund et al (1989) *Plant Physiol.* 88: 47. Briefly, SDS-PAGE gels were electroblotted onto nitrocellulose filters, which were then incubated with antiserum (1:1500 dilution). Antigen was visualized by the conjugated-horseradish peroxidase assay following secondary incubation with goat anti-rabbit IgG (Promega).

Results

Cellulase cDNA clones were isolated from a pepper pericarp cDNA library by screening replicate filters containing a total of 450,000 clones with the three probes described above. Twenty-nine independent cDNA clones were isolated using this screening method and each of these was characterized by detailed restriction enzyme analysis and dideoxy sequence analysis. Based upon this characterization, all such cDNA clones were determined to have the same primary nucleotide sequence within the region where they overlapped and hence were most likely derived from the transcription of a single gene, designated PCEL1.

The two longest cDNAs, pCP35-5 and pCP40A, were complely sequenced (both strands) and found to encode an ORF specifying a 506 amino add polypeptide (Mr of 55,765 and isoelectric of 8.25) with 89.27% amino acid identity and 93.93% similarity to the protein predicted by the tomato Cell gene. Computer alignment with tomato Cel2 (Lashbrook et al (1994) op.cit; 47.23% identity and 77.87% similarity), a bean abscission cellulose (Tucker and Millisan (1991) *Plant Physiol* 95: 928; 68–53% identity and 79.79% similarity), a soybean abscission cellulase (Kemmerer and Tucker (1994) *Plant Physiol.* 104: 557; 68–01% identity and 77.78% similarity) and an avocado fruit cellulase (Tucker et al. (1987) *Plant Mol. Biol.* 9: 197; 51–67% identity and 68.54% similarity) was considerably less. Salient features of the translated polypeptide include a hydrophobic N-terminus characteristic of signal sequences (von Heijne (1986) *Nucl. Acids Res.* 14: 4683, and 3 glycosylation consensus motifs (Asn-X-Ser/Thr).

At their 5' ends, pCP35-5 and pCP40A extend 204 and 315 bases, respectively, beyond the translation start codon, which is indicative of a long 5' untranslated leader for the PCEL1 transcript. Sequence analysis of 3' ends again demonstrated colinearity of all cDNAs.

In an effort to isolate and characterize the PCEL1 promoter sequence, a pepper genomic library was screened with PCEL1 riboprobe. A total of four hybridizing phage clones were isolated, all of which were overlapping and exhibited absolute sequence identity with the PCEL1 cDNAs for sequence 5' to the ATG initiation codon. Downstream of the start codon, however, several intron/exon splice junctions were identified which indicated conservation of intron sites with those reported for the Cel1 gene of avocado (data not shown). Additional PCEL1 5' sequence obtained from the characterization of these clones enabled the identification of putative TATA and CCAAT boxes as well as sequence proximal to the transcription start site. A unique sequence identified within the 5' flanking region consists of a 69 bp direct repeat (81% identity) having no significant homology to sequences registered in the databank (NIH BLAST program). The sequence derived from the genomic clone and the cDNA clones is shown in FIG. 1.

Example 2

Pepper Fruit with Diminished Levels of Hemicellulase Gene

A sense suppression construct was generated in the following manner.

In order to prepare the PCEL1 coding region for reintroduction and expression in plants, the coding region was modified by the addition of restriction enzyme cleavage sites at the translation start and adjacent to the translation stop. These sites allowed for the simple excision of the coding region from the cDNA clone and the subsequent fusion of the PCEL1 coding region to appropriate transcriptional control regions. Specifically, an NcoI site was introduced at the translation start using oligonucleotide site-directed mutagenesis with the following oligonucleotide:

Oligo #3 5' ATATATATAACCATGGCTTG 3'

A BglII site was introduced adjacent to the translation stop using the following oligonucleotide:

Oligo #4 5' AAATTGAAGATCTATAGTC 3'

The PCEL1 coding region was isolated from the plasmid pCP35M by digestion with NcoI and BglII, and then inserted into the plasmid pJJ2104 (Harpster et al., 1988 *Mol. Gen. Genet.* 212:182–190) which had been digested with NcoI and BamHI. The resulting plasmid, pJJ2104C1, was composed of the complete PCEL1 coding region fused to the CaMV 35S promoter at the 5' end, and the nos terminator at the 3' end. In addition to the fusion of the full length PCEL1 coding region to the CaMV35S promoter and nos terminator, a truncated form was constructed using an existing NcoI restriction site 240 nucleotides downstream from the translation start and this 5' truncated coding region was fused to the same promoter and terminator fragments. This plasmid was termed pJJ2104C1delta10.

The PCEL1 coding region (either full length or truncated), flanked by the CaMV35S promoter and the nos terminator, was isolated after BglII and HindIII digestion of the plasmids pJJ2104C1 or pJJ2104C1delta10, followed by the generation of blunt termini with Klenow enzyme, and then inserted into the SmaI digested binary vectors pWTT2055 or pWTT2132 (respectively). The resulting plasmid pJJ2104C1/pWTT2055 carried the full length PCEL1 coding region flanked by the CaMV35S promoter and the nos terminator, adjacent to the NPTII selectable marker for tomato transformation and between the left and right borders of T-DNA which direct insertion into the plant genome during transformation (see Example 3 below). The plasmid pJJ2104C1delta10/pWTT2132 carried the truncated PCEL1 coding region flanked by the CaMV35S promoter and the nos terminator, adjacent to the ALS selectable marker for pepper transformation, and between the left and right borders of T-DNA which direct insertion into the plant genome. This latter plamid was used exclusively for pepper transformation in accordance with Example 2 of U.S. Pat. No. 5,262,316 in order to generate pepper plants with reduced Cel1 levels in the fruit. The pJJ2104C1/pWTT2055 plamid was used for the generation of tomato transformants (Example 3).

Transformants obtained by transformation in accordance with the method disclosed in Example 1 of U.S. Pat. No. 5,262,316, incorporated herein by reference, were screened initially at the enzyme activity level and/or the protein level by Western blotting. The transgenic plants were allowed to set fruit and once the fruit were at the red ripe stage, pericarp protein extracts were prepared and the hemicellulase activity was measured in the transformants and in fruit from control plants or the level of Cel1 protein was determined by Western blot. In excess of 80 pepper transformants were screened in this way, some of which carried the full length PCEL1 coding region, and the majority of which carried the truncated PCEL1 coding region. Several independent primary transformants were obtained with varying levels of PCEL1 suppression. One particular primary transformant in which hemicellulase activity was absent in the ripe fruit was identified for further investigation. Furthermore, immunological analysis indicated that the PCEL1 protein was absent in the fruit. This suppressed line was assigned the number B13a. Through conventional breeding of this primary transformant, homozygous suppressed T2 lines B13a-8 and B13a-18 were developed.

Figure 3:
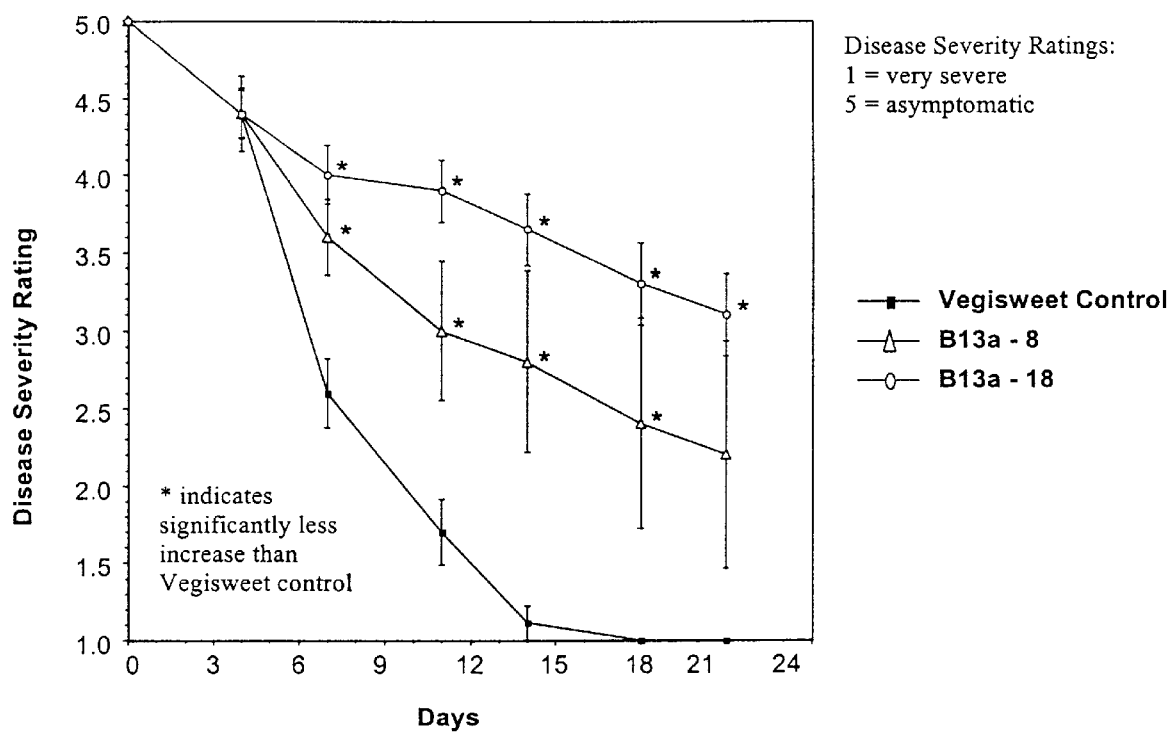
FIG. 3 shows the enhanced disease resistance to Alternaria infection for pepper lines suppressed with a Capsicum hemicellulase suppression transgene (lines B13a-8 and B13a-18) as compared to control (Vegisweet).

Fruit from these lines was found to have endo-1,4-β-glucanase levels reduced by at least 95% relative to parental control material lacking a sense suppression construct. The fruit of each of these lines exhibited increased disease resistance to *Alternaria alternata* infection in the fruit, increased shelf life, and increased crispness as measured by Instron measurements. These lines of suppressed pepper have a storage life at 4° C. of approximately 10–15 days longer than controls. An example of the storage life enhancement of the B13a line as compared to control is shown graphically in FIG. 2. An example of the suppressed peppers enhanced resistance to disease (Alternaria) is shown in FIG. 3. Table I shows the crispness measurements (12 days after harvest) as determined on an Istron; higher values indicate more firmness.

TABLE I

| | Crispness Measurement | | |
|---|---|---|---|
| Line | Suppressed? | Mean Crispness Value | Std. Error |
| B13a-8 | Y | 1.641 | 0.042 |
| B13a-18 | Y | 1.512 | 0.025 |
| VS300 | N | 1.256 | 0.020 |

Example 3

Tomato Fruit with Enhanced Levels of Hemicellulase Gene

The construct pJJ2104C1/pWTT2055, which contains a complete PCEL1 coding region, was introduced into tomato by *A. tumefaciens* transformation of tomato cotyledon explants in accordance with the following method.

The plasmid pJJ2104C1/pWTT2055 (with pWTT2055 as control) was used in the transformation of tomato cultivar Bonny Best. Transformation of tomato cotyledons was conducted by standard methods using Agrobacterium as described below.

All manipulations were carried out under sterile conditions. A culture of Agrobacterium LBA4404 containing the plasmid was grown for 24 hours in minimal A medium at 28° C. Explants were excised from the midsections of 7–8 day old cotyledons of sterilely grown *L. esculentum* seedlings on germination medium. The Agrobacterium culture was diluted in liquid 2% glucose-OMS to a final concentration of $5 \times 10^5$/ml.

The explants were submerged in the Agrobacterium suspension for 20–30 minutes and then placed on cocultivation plates for 2 days at 25° C. The cocultivation was terminated by washing the leaf discs in liquid 2% glucose-Oms for 2 hours. The explants were then placed on solid selective regeneration media and cultured under high light fluence with an 8 hour dark period at 25° C. After 10 days Kanamycin resistant callus appeared and then small shoot buds by 3 weeks. At 5 weeks the healthy calli and shoots were transferred to fresh selection regeneration medium and within 2 weeks many transformed shoots emerged. The shoots were then excised and transferred to selective rooting medium. Plants that successfully developed shoots in this medium in 6–10 days were all transformants. These plants were then transferred to non-selective rooting medium for 2 weeks to check for residual Agrobacteria, then transplanted to soil. Approximately 100 independent transformants were regenerated in each cultivar.

The measurement of expression of the introduced and endogenous hemicellulase gene was through direct quantitation of mRNA levels using the RNase protection method. A probe fragment was prepared from the PCEL1 gene which encompassed 230 bases of the pepper PCEL1 coding region. This probe detected messenger of the introduced gene as a 230 base pair fragment. A separate probe was prepared for the detection of messenger of the endogenous tomato Cel1 gene. The probe fragment was prepared from the pFW-TC4 plasmid and corresponded to 470 bases from the coding region. This probe detected expression of messenger of the endogenous gene as a 470 base fragment. The results of these expression studies are summarized in Table II.

In Table II, transformant 1 is the control (transformed under same conditions but without presence of Cel1 gene). Readouts of messenger level are on a five-step scale with the lowest level (not detected) being "−;" intermediate levels in ascending order being "±," "+," and "++;" and the highest level (full expression corresponding to endogenous levels in the control) being "+++." That is, these levels correspond to approximate levels of 0, 25, 50, 75 and 100% as compared to endogenous levels in the control. There were no plants numbered 11, 12 or 13.

TABLE II

Hemicellulase mRNA in Tomato

| Transformant | Endogenous | Transgene |
|---|---|---|
| 1 | +++ | − |
| 2 | ++ | +++ |
| 3 | +++ | +++ |
| 4 | +/− | + |
| 5 | +/− | − |
| 6 | ++ | ++ |
| 7 | +/− | + |
| 8 | ++ | − |
| 9 | + | +++ |
| 10 | + | ++ |
| 14 | ++ | +++ |
| 15 | ++ | − |
| 16 | + | − |
| 17 | − | − |
| 18 | + | − |
| 19 | − | − |

The above data indicate that the introduction of the PCEL1 gene (transgene) results in a reduction in the level of expression of the corresponding tomato Cel1 gene (endogenous) in all the transformants tested except for one (transformant 3).

A screen of the transformants for hemicellulase activity showed that, in one line, the pepper PCEL1 gene in the transgene construct is expressed in the tomato at high levels, resulting in an increase in endo-1,4-β-glucanase of several hundred-fold compared to controls. These tomato fruit were found to have a significant increase in soluble solids (Brix). Brix values correspond to refractometer readings taken on filtered slurries made from the fruit at the red stage. The Brix measurements increased from 4.5 (=4.5% total soluble solids) in control fruit, to 5.1 (=5.1% total soluble solids) in the transgenic overexpressors of Cel1. The transgenic fruit also had significantly increased titratable acidity. Red fruit slurries were titrated against 1N NaOH until the pH 8.2, and the amount of added NaOH to reach this endpoint is standardly used to determine the titratable acidity (TA). Control fruit were measured routinely at a TA of 4.8 while Cel1 overexpressors had TAs of 0.66–0.72. HPLC analysis of these extracts demonstrated that the increased acidity arises from increased citric acid levels.

The transgene encoded Capsicum hemicellulase gene was found to be expressed in the pericarp and leaf tissue of the tomato.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

We claim:

1. An isolated Capsicum hemicellulase polynucleotide which comprises a polynucleotide sequence that encodes at least 50 amino acids of a Capsicum hemicellulase polypeptide that has the amino acid sequence shown in SEQ ID NO: 2.

2. The isolated Capsicum hemicellulase polynucleotide of claim 1, wherein the polynucleotide comprises at least 100 consecutive nucleotides which are at least 95% identical to the polynucleotide sequence of SEQ ID NO:1.

3. The isolated Capsicum hemicellulase polynucleotide of claim 2, wherein the polynucleotide comprises the polynucleotide sequence of SEQ ID NO:1.

4. A polynucleotide construct comprising a Capsicum hemicellulase polynucleotide operably linked to a heterologous promoter which drives transcription in pepper, wherein expression of said polynucleotide construct in pepper results in increased hemicellulase activity or suppression of endogenous hemicellulase expression.

5. The polynucleotide construct of claim 4, wherein the Capsicum hemicellulase polynucleotide comprises the sequence of SEQ ID NO:1.

6. The polynucleotide construct of claim 4, wherein the heterologous promoter is a CaMV 35S promoter.

7. The Capsicum hemicellulase polynucleotide of claim 1 localized in the genome of a Lycopersicon plant.

8. A tomato plant comprising a genome having at least one integrated copy of a Capsicum hemicellulase polynucleotide, wherein said polynucleotide is expressed and encodes a polypeptide having hemicellulase activity.

9. A pepper plant having a genome comprising a copy of a Capsicum hemicellulase polynucleotide operably linked to a heterologous promoter.

10. A tomato having increased solids content, wherein said tomato contains a Capsicum hemicellulase polypeptide expressed in a somatic cell.

11. A plant comprising a heterologous Capsicum hemicellulase polynucleotide expressed in a somatic cell of a fruit, wherein expression of the heterologous Capsicum hemicellulase polynucleotide results in supression of endogenous hemicellulase activity.

12. A pepper plant having a genome with a Capsicum hemicellulase polynucleotide integrated in a position other than a naturally occurring Capsicum hemicellulase gene locus.

13. A seed of the plant of claim 9, claim 11, or claim 12.

14. A fruit of the plant of claim 9, claim 11, or claim 12.

15. A cultivated Lycopersicon plant exhibiting altered ripening, said plant comprising at least one cell transformed with a Capsicum hemicellulase DNA segment operably linked to a promoter in the sense orientation, wherein said hemicellulase DNA segment comprises at least 50 base pairs having at least 85% identitity to the polynucleotide of SEQ ID NO:1.

* * * * *